(12) United States Patent
Kohgo et al.

(10) Patent No.: US 11,752,180 B2
(45) Date of Patent: *Sep. 12, 2023

(54) INTESTINAL PROTECTANT

(71) Applicants: National University Corporation Asahikawa Medical University, Asahikawa (JP); Sapporo Holdings Limited, Tokyo (JP)

(72) Inventors: Yutaka Kohgo, Tokyo (JP); Mikihiro Fujiya, Asahikawa (JP); Nobuhiro Ueno, Asahikawa (JP); Syuichi Segawa, Tokyo (JP); Naoyuki Kobayashi, Tokyo (JP)

(73) Assignees: National University Corporation Asahikawa Medical University, Hokkaido (JP); Sapporo Holdings Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/986,621

(22) Filed: Aug. 6, 2020

(65) Prior Publication Data

US 2020/0368299 A1    Nov. 26, 2020

Related U.S. Application Data

(63) Continuation of application No. 13/639,206, filed as application No. PCT/JP2011/057689 on Mar. 28, 2011, now Pat. No. 10,792,315.

(30) Foreign Application Priority Data

Apr. 8, 2010 (JP) ................. 2010-089469

(51) Int. Cl.
| | |
|---|---|
| A61K 35/747 | (2015.01) |
| A61K 33/42 | (2006.01) |
| A23L 2/52 | (2006.01) |
| A23L 33/16 | (2016.01) |
| A23L 33/10 | (2016.01) |
| A23L 33/135 | (2016.01) |

(52) U.S. Cl.
CPC .............. *A61K 35/747* (2013.01); *A23L 2/52* (2013.01); *A23L 33/10* (2016.08); *A23L 33/135* (2016.08); *A23L 33/16* (2016.08); *A61K 33/42* (2013.01); *A23V 2002/00* (2013.01)

(58) Field of Classification Search
CPC ....... A61K 35/747; A61K 33/42; A23L 33/10; A23L 33/16; A23L 33/135; A23L 2/52; A23V 2002/00
USPC .................................................... 424/93.45
See application file for complete search history.

(56) References Cited

U.S. PATENT DOCUMENTS

| | | |
|---|---|---|
| 2006/0177517 A1 | 8/2006 | Shiba et al. |
| 2009/0285886 A1 | 11/2009 | Van Beek |
| 2009/0285904 A1 | 11/2009 | Van Beek |
| 2011/0220570 A1 | 9/2011 | Ruiz |

FOREIGN PATENT DOCUMENTS

| | | |
|---|---|---|
| EP | 2119363 A2 | 11/2009 |
| JP | 2002-504324 A | 2/2002 |
| JP | 2006-006264 A | 1/2006 |
| JP | 2006-176450 A | 7/2006 |
| JP | 2007-169171 A | 7/2007 |
| JP | 2007-195401 A | 8/2007 |
| JP | 2007-291042 A | 11/2007 |
| JP | 2008-212006 A | 9/2008 |
| JP | 2008-266215 A | 11/2008 |
| JP | 2010-083881 A | 4/2010 |
| WO | 2004/075906 A1 | 9/2004 |
| WO | 2004/110462 A1 | 12/2004 |
| WO | 2008/023663 A1 | 2/2008 |
| WO | 2009/104005 A1 | 8/2009 |

OTHER PUBLICATIONS

Antoni et al., "Intestinal barrier in inflammatory bowel disease," World Journal of Gastroenterology, 20 (5): 1165-1179 (2014).
Office Action issued in Japanese Patent Application No. 2012-509466 dated Jun. 3, 2014.
Kang et al., "Suppressive effect of non-anaphylactogenic anti-IgE antibody on the development of dextran sulfate sodium-induced colitis," International Journal of Molecular Medicine, 18(5): 893-899 (2006).
Extended European Search Report issued in European Patent Application No. 11765519.1 dated Jul. 19, 2013.
Segawa et al., "Probiotic-Derived Polyphosphate Enhances the Epithelial Barrier Function and Maintains Intestinal Homeostasis through Integrin-p38 MAPK Pathway," PLOS One, 6(8): e23278 (2011).
Barbatis et al., "Heat Shock Proteins in Inflammatory Bowel Disease," Annals of Gastroenterology, 22 (4): 244-247 (2009).
Centers for Disease Control and Prevention, Inflammatory Bowel Disease, Accessed Jun. 19, 2013, online at www.cdc.gov/ibd/.
Shiba et al., "Modulation of Mitogenic Activity of Fibroblast Growth Factors by Inorganic Polyphosphate," The Journal af Biological Chemistry, 278 (29): 26788-26792 (2003).
Matsuura et al., "Therapeutic Effects of Rectal Administration of Basic Fibroblast Growth Factor on Experimental Murine Colitis," Gastroenterology, 128: 975-986 (2005).
Fujiya et al., "The Bacillus subtilis Quorum-Sensing Molecule CSF Contributes to Intestinal Homeostasis via OCTN2, a Host Cell Membrane Transporter," Cell Host & Microbe, 1: 299-308 (2007).
International Search Report issued in corresponding International Patent Application No. PCT/JP2011/057689 dated May 17, 2011.
International Preliminary Report on Patentability issued in corresponding International Patent Application No. PCT/JP2011/057689 dated Nov. 15, 2012.
Written Opinion issued in corresponding International Patent Application No. PCT/JP2011/057689 dated May 17, 2011.

*Primary Examiner* — Jennifer M. H. Tichy
(74) *Attorney, Agent, or Firm* — Morgan, Lewis & Bockius LLP

(57) ABSTRACT

The present invention provides an intestinal tract protective agent comprising a polyphosphoric acid or a pharmaceutically acceptable salt thereof as an active ingredient.

24 Claims, 17 Drawing Sheets
Specification includes a Sequence Listing.

Fig.2
(A)
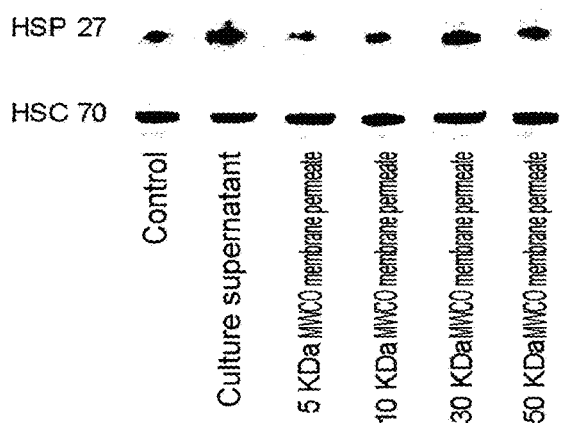
(B)
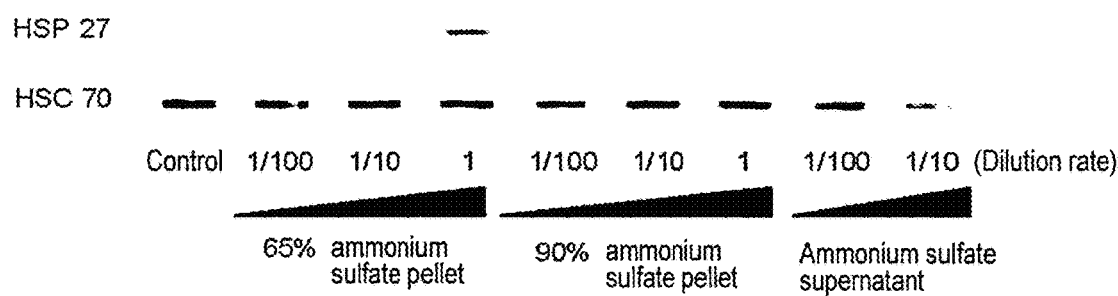

Fig.3
(A)
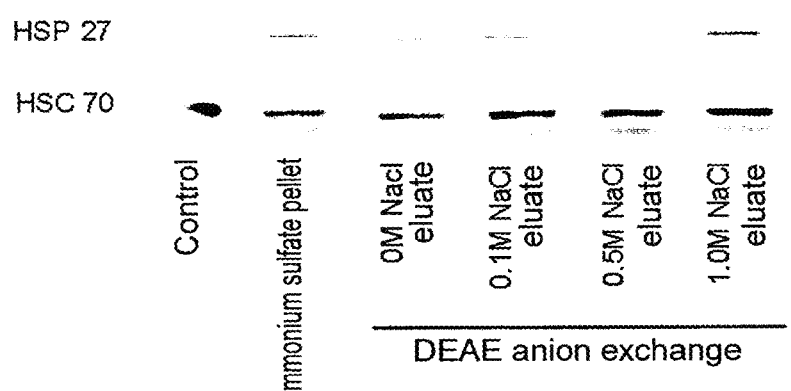
(B)
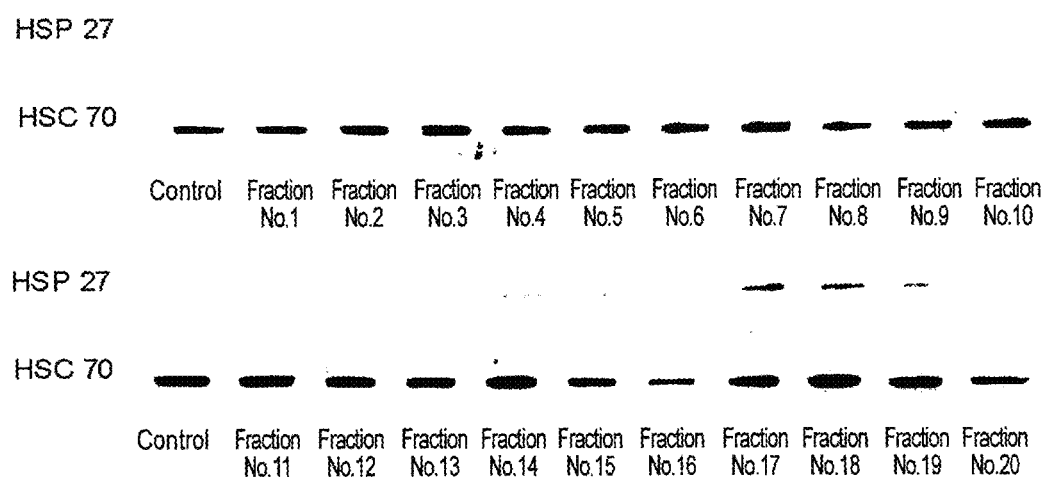

*Fig.4*
(A)
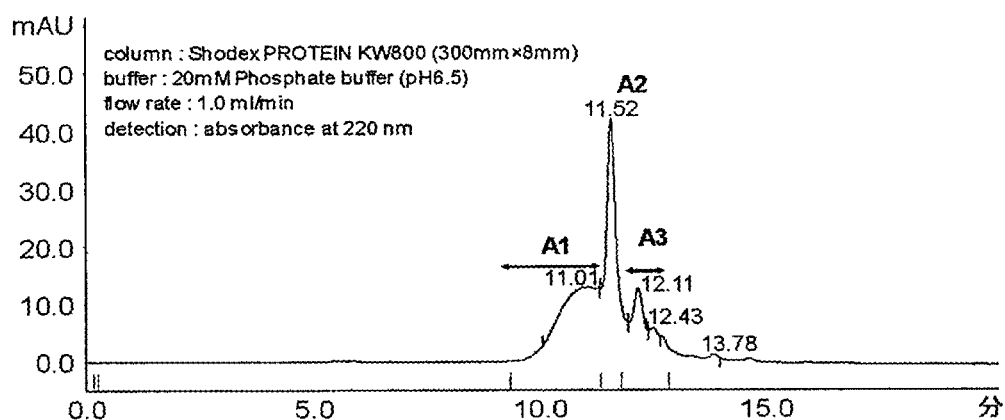
(B)
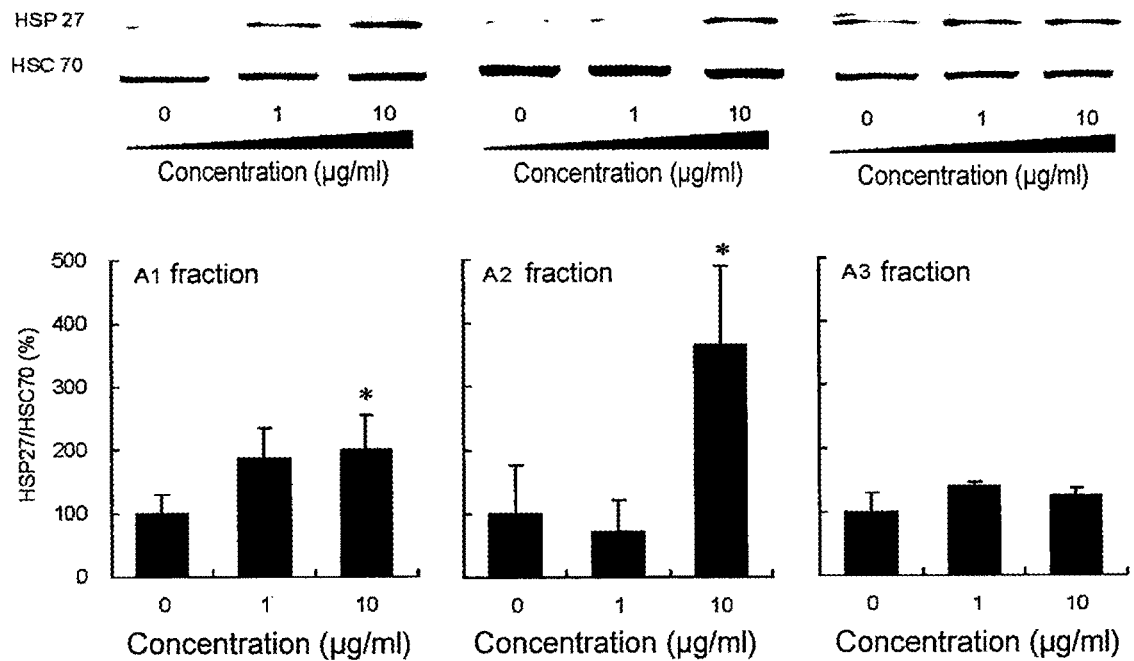

INTESTINAL PROTECTANT

SEQUENCE LISTING SUBMISSION VIA EFS-WEB

A computer readable text file, entitled "SequenceListing.txt," created on or about Jul. 23, 2020 with a file size of about 1 kb contains the sequence listing for this application and is hereby incorporated by reference in its entirety.

TECHNICAL FIELD

The present invention relates to an intestinal protectant (intestinal tract protective agent).

BACKGROUND ART

The intestinal tract of the mammals has a barrier function (intestinal tract barrier function) to protect a living body from harmful microorganisms, toxins, etc. However, when the intestinal tract barrier function is broken down for some reasons, the chaotic invasion of harmful microorganisms, toxins, etc. into a living body occurs which can cause various diseases. For example, it has been considered that the decline of intestinal tract barrier function is responsible for developing diseases in the intestinal tract such as inflammatory bowel diseases (Crohn's disease, ulcerative colitis) and alcoholic liver damage.

Up to date, as substances which suppress the decline of intestinal tract barrier function, lipoteichoic acid produced by *Lactobacillus rhamnosus* OLL2838 strain (Patent Literature 1) and pentapeptide produced by *Bacillus subtilis* are reported.

CITATION LIST

Patent Literature

Patent Literature 1: Japanese Patent Application Laid-Open No. 2008-212006

Non-Patent Literature

Non-patent Literature 1: Cell Host Microbe., 2007, Vol. 1, pp. 299-308

SUMMARY OF INVENTION

Problems to be Solved by the Invention

The intestinal tract protective agent, which is capable of protecting the intestinal tract by suppressing the decline of intestinal tract barrier function or recovering the declined intestinal tract barrier function, is considered to be effective to prevent or ameliorate (treat, alleviate) various bowel diseases accompanied with the decline of intestinal tract barrier function. Some intestinal tract protective agents as such are known but, in reality, it is difficult to say that there are enough selections to meet a wide variety of demands from consumers.

Thus, the present invention has an object of providing a novel intestinal tract protective agent.

Means for Solving the Problems

The present invention provides an intestinal tract protective agent comprising a polyphosphoric acid or a pharmaceutically acceptable salt thereof as an active ingredient.

The intestinal tract protective agent of the present invention can suppress the decline of intestinal tract barrier function and recover the function of intestinal tract barrier function by containing a polyphosphoric acid or an a pharmaceutically acceptable salt thereof as an active ingredient. The intestinal tract protective agent of the present invention can protect the intestinal tract through these actions.

The intestinal tract protective agent of the present invention, since it works based on the above action mechanisms, is capable of preventing or ameliorating (treating, alleviating) inflammatory bowel diseases (Crohn's disease, ulcerative colitis) through the suppression of decline in intestinal tract barrier function or the recovery of intestinal tract barrier function.

The intestinal tract protective agent of the present invention, owing to the above effects it renders, for example, can be used to suppress the decline of intestinal tract barrier function or can be used to recover the intestinal tract barrier function. Also, the intestinal tract protective agent of the present invention can be used as an agent for preventing or ameliorating inflammatory bowel diseases (Crohn's disease, ulcerative colitis).

The intestinal tract protective agent of the present invention can also induce the expression of heat shock protein (HSP) 27 by containing a polyphosphoric acid or a pharmaceutically acceptable salt thereof as an active ingredient. At least a part of the above action mechanisms rendered by the intestinal tract protective agent of the present invention is based on this HSP 27 expression induction.

The intestinal tract protective agent of the present invention can be used as a pharmaceutical product component, food or beverage component, food or beverage additive, feed component, feed additive, etc.

The present invention further provides a microorganism which produces the above polyphosphoric acid used to suppress the decline of intestinal tract barrier function or to recover the intestinal tract barrier function. The microorganism of the present invention produces the above polyphosphoric acid and hence can be used to suppress the decline of intestinal tract barrier function or to recover the intestinal tract barrier function. Similarly, the microorganism produces the above polyphosphoric acid and hence can be used to prevent or ameliorate inflammatory bowel diseases.

It is preferred that the above microorganism be a lactic acid bacterium (*lactobacillus*). A lactic acid bacterium survives or grows in the intestines and is capable of continuously supplying the polyphosphoric acid in the intestines, rendering higher effects.

The lactic acid bacterium may be *Lactobacillus brevis* SBC8803 strain. *Lactobacillus brevis* is a species of lactic acid bacteria which has been used in the fermented food products for a long time and the safety thereof to the living body is established. For this reason, it can be consumed continuously for an extended period of time. *Lactobacillus brevis* SBC8803 strain is a strain which has been deposited on Jun. 28, 2006 with the International Patent Organism Depositary, the National Institute of Advanced Industrial Science and Technology (Central 6, 1-1, Higashi 1-chome, Tsukuba-shi, Ibaraki-ken, Japan (zip code 305-8566)) under accession No. FERM BP-10632.

Further, the microorganism of the present invention can be used as a pharmaceutical product component, food or beverage component, food or beverage additive, feed component, feed additive, etc.

As described above, the polyphosphoric acid or a pharmaceutically acceptable salt thereof or the above microorganism can be used to protect the intestinal tract or to suppress the decline of intestinal tract barrier function or to recover the intestinal tract barrier function. Furthermore, the polyphosphoric acid or a pharmaceutically acceptable salt thereof or the above microorganism can be used to prevent or ameliorate inflammatory bowel diseases (Crohn's disease, ulcerative colitis).

More specifically, the present invention also provides a method for protecting the intestinal tract by administering an effective amount of the polyphosphoric acid or a pharmaceutically acceptable salt thereof or the above microorganism. Further, the present invention provides a method for suppressing the decline of intestinal tract barrier function or recovering the intestinal tract barrier function by administering an effective amount of the polyphosphoric acid or a pharmaceutically acceptable salt thereof or the above microorganism. Furthermore, the present invention also provides a method for preventing or ameliorating inflammatory bowel diseases (Crohn's disease, ulcerative colitis) by administering an effective amount of the polyphosphoric acid or a pharmaceutically acceptable salt thereof or the above microorganism.

Effects of the Invention

According to the present invention, a novel intestinal tract protective agent comprising a polyphosphoric acid or a pharmaceutically acceptable salt thereof as an active ingredient is provided. The intestinal tract protective agent of the present invention can protect the intestinal tract by suppressing the decline of intestinal tract barrier function and by recovering the intestinal tract barrier function. Also, inflammatory bowel diseases can be effectively prevented or ameliorated through these actions.

BRIEF DESCRIPTION OF THE DRAWINGS

FIG. 2 is pictures of western blot showing the separation of HSP 27 expression inducing substances in Example 2;

FIG. 3 is pictures of western blot showing isolation state at each process in the isolation of HSP 27 expression inducing substances in Example 3;

FIG. 4 is an HPLC chart and pictures of western blot showing isolation state at each process in the isolation of HSP 27 expression inducing substances in Example 3;

EMBODIMENTS FOR CARRYING OUT THE INVENTION

Figure 1:
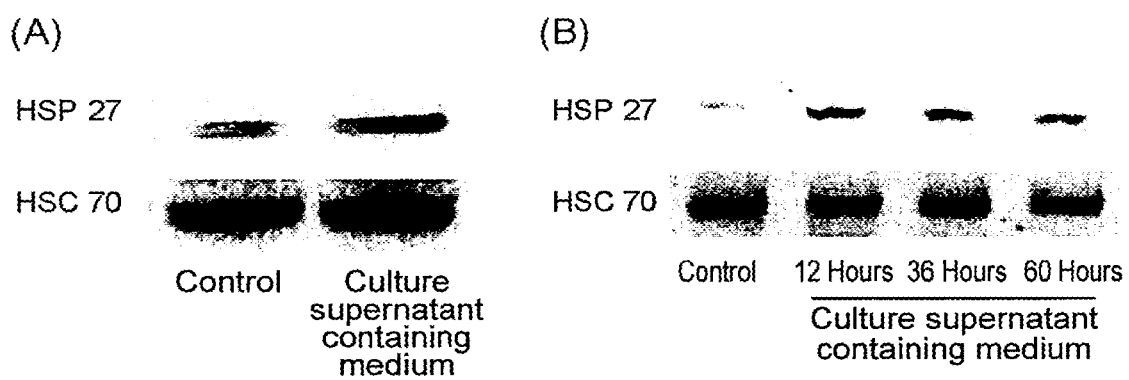
FIG. 1 is pictures of western blot showing the expression induction of HSP 27 in Example 1.

The intestinal tract protective agent of the present invention comprises a polyphosphoric acid or a pharmaceutically acceptable salt thereof as an active ingredient.

The present inventors found that, in an inflammatory bowel disease model mouse in which an acute enteritis is induced by dextran sulfate sodium (DSS), the mortality can be significantly reduced by suppressing the decline of intestinal tract barrier function and by recovering the function of intestinal tract barrier function using a polyphosphoric acid. The present inventors also found that, in the intestinal epithelium cell, the expression of HSP 27 is induced by the polyphosphoric acid. The present invention has been accomplished based on these novel findings.

Accordingly, the intestinal tract protective agent in the present embodiment may be used to suppress the decline of intestinal tract barrier function or to recover the function of intestinal tract barrier function. More specifically, the intestinal tract protective agent may be used to prevent or ameliorate bowel diseases caused by the decline of intestinal tract barrier function.

The polyphosphoric acid in the present specification means a condensed phosphoric acid compound wherein phosphoric acid ($H_3PO_4$) is dehydro-condensed. Examples of such a condensed phosphoric acid compound include a chain polyphosphoric acid in which phosphoric acids are linked to form a chain and a cyclic polyphosphoric acid in which both ends bond to each other. Also, examples of the chain polyphosphoric acid include a linear chain polyphosphoric acid having no branch and a branched chain polyphosphoric acid having a branch.

The linear chain polyphosphoric acid herein can be represented by formula (1). In formula (1), n represents 0 or a natural number. Examples of the branched chain polyphosphoric acid include those in which a linear chain polyphosphoric acid having no branch or a branched chain polyphosphoric acid having a branch further bonds to the side chain of the linear chain polyphosphoric acid represented by formula (1).

[Chemical Formula 1]

$$HO-\overset{O}{\underset{OH}{\overset{\|}{P}}}-O-\left[\overset{O}{\underset{OH}{\overset{\|}{P}}}-O\right]_n-\overset{O}{\underset{OH}{\overset{\|}{P}}}-OH \quad (1)$$

In formula (1), it is preferred that n be 10 or more, it is more preferred that n be 50 or more, and it is further preferred that n be 100 or more. Use of such a high polymer polyphosphoric acid can more effectively provide the decline suppression action on the intestinal tract barrier function and the function recovery action on the intestinal tract barrier function through which the intestinal tract can be protected more effectively. Also, inflammatory bowel diseases can be more effectively prevented or ameliorated (treated, alleviated). On the other hand, n can be 10,000 or less in view of easy handling, although the upper limit of n is not limited.

It is preferred that the polyphosphoric acid of the present embodiment be a high polymer polyphosphoric acid which does not permeate a ultrafiltration membrane with a molecular weight cut off of 10 kDa when the ultrafiltration is carried out. The ultrafiltration in the present specification means that molecules in a sample to be filtered are screened, using a spin column equipped with an ultrafiltration membrane composed of PES (polyethersulfone), by adding the sample to be filtered to the spin column followed by centrifugal separation.

The intestinal tract protective agent of the present embodiment may comprise the above polyphosphoric acid in the form of a pharmaceutically acceptable salt. Such a pharmaceutically acceptable salt is the one formed by a polyphosphoric acid and a base forming a nontoxic salt. Specific examples include, but are not particularly limited to, alkali metal salts such as sodium salt and potassium salt, alkaline earth metal salts such as magnesium salt and calcium salt, and ammonium salts.

Also, the intestinal tract protective agent of the present embodiment may comprise a plurality of the active ingredient selected from the group consisting of the above polyphosphoric acid and pharmaceutically acceptable salts thereof.

The method for producing the polyphosphoric acid is not particularly limited, but may be a method which includes at least a synthesis step of synthesizing a polyphosphoric acid using adenosine triphosphate (ATP) as a starting material. The method may also include a purification step of purifying the synthesized polyphosphoric acid.

In the synthesis step, the polyphosphoric acid may be chemically synthesized, synthesized in vitro using a biomolecule such as an enzyme, or synthesized using a microorganism, etc. which produces the polyphosphoric acid. When a linear chain polyphosphoric acid is synthesized, it is preferred that it be synthesized in vitro using a biomolecule such as an enzyme or synthesized using a microorganism, etc. since a linear chain polyphosphoric acid can be obtained highly efficiently.

An example of the method for chemically synthesizing the polyphosphoric acid is a method in which a reaction solution containing ATP as a starting material is heated and dehydro-condensed. The heating temperature may be, for example, from 150 to 350° C.

An example of the method for synthesizing a polyphosphoric acid in vitro using a biomolecule such as an enzyme is a method in which a polyphosphoric acid is synthesized, using as the "biomolecule such as an enzyme" polyphosphate kinase (PPK) which is a polyphosphoric acid-synthesizing enzyme, by the enzymatic action of PPK with ATP as a starting material. Many probiotics such as *Lactobacillus rhamnosus* GG strain and strains belonging to *Lactobacillus brevis* are reported to contain PPK and the gene sequence of the enzyme is publicly available at the DB.

PPK may be those capable of synthesizing a polyphosphoric acid using ATP as a substrate and can be obtained from any strains expressing PPK or a commercial product may be purchased. PPK may be the PPK derived from *Propionibacterium shermanii*, for example.

The enzymatic reaction by PPK is reversible but, when a larger amount of ADP is present than that of ATP in the reaction solution, the decomposition reaction of a polyphosphoric acid prevails so that an ADP/ATP ratio reaches equilibrium. Thus, for efficient synthesis of a polyphosphoric acid, it is preferred that ADP be not added to the reaction solution. Other conditions such as reaction solution composition, reaction temperature, reaction time, etc., may be suitably set in accordance with synthesis scale, etc., to be optimum for the PPK activity. An example of the reaction conditions in the case where a polyphosphoric acid is synthesized using a *Propionibacterium shermanii*-derived PPK is given as follows. A reaction solution composition may contain 50 mM Tris-HCl (pH 7.4), 40 mM ammonium sulfate, 4 mM $MgCl_2$, 40 mM creatine phosphate, 20 ng/ml creatine kinase, 1 mM ATP (pH 7.2) and 1 U/ml PKK, the reaction temperature may be 37° C. and the reaction time may be 0.5 to 10 hours. The reaction time may be suitably set in accordance with the molecular weight and yield of an intended polyphosphoric acid, and, for example, it is preferred that the reaction time be 1 to 5 hours to obtain a high molecular weight polyphosphoric acid in a good yield.

An example of the synthesis method using a microorganism, etc. is a method in which a polyphosphoric acid-producing microorganism is cultured under suitable culture conditions to allow the microorganism produce the polyphosphoric acid. Examples of the polyphosphoric acid-producing microorganism include *Lactobacillus rhamnosus* GG strain, *Lactobacillus brevis* SBC8803 strain, strains belonging to genera *Lactobacillus, Bifidobacterium, Enterococcus, Lactococcus, Pediococcus, Leuconostoc, Streptococcus, Bacteroidetes, Eubacterium*, and *Clostridium*.

A polyphosphoric acid may be synthesized by culturing the above microorganism in suitable medium capable of sustaining the growth of the microorganism to be used under a suitable culture temperature condition. The synthesized polyphosphoric acid may be collected from the medium after the culture or collected by fragmenting the microorganism after the culture.

In the purification step of the synthesized polyphosphoric acid, purification methods commonly used in this technical field such as the size exclusion chromatography, ion exchange chromatography, affinity chromatography, high performance liquid chromatography (HPLC), dialysis, salting out, ammonium sulfate precipitation, precipitation, crystallization, etc., may be suitably used in combination. The purification method used may be suitably determined in accordance with the method used in the synthesis step of the polyphosphoric acid, an intended purity, an intended yield, etc.

An example of the purification step is described. After the synthesis step, $CaCl_2$ is added to the reaction solution to aggregate the synthesized polyphosphoric acid and the solution is subjected to the centrifugal separation to collect the precipitate of calcium polyphosphate. The precipitate is dissolved in an EDTA solution and dialyzed using a dialysis membrane. A purified solution of the synthetic polyphosphoric acid from which low weight molecules have been removed by dialysis is obtained. The purified solution of the synthetic polyphosphoric acid may further be fractionated based on the molecular weight, charge, etc., using chromatography such as HPLC, etc. Thus, for example, a synthetic polyphosphoric acid of a desired molecular weight range may be obtained.

The intestinal tract protective agent of the present invention may be in any form of solids (for example, a powder obtained by freeze drying), liquids (a water soluble or liposoluble solution or suspension), pastes, etc., or may be in any dosage form of powders, granules, tablets, syrups, trochiscuses, capsules, etc.

Each of the above preparation may comprise, in addition to the polyphosphoric acid or a pharmaceutically acceptable salt thereof, additives which are routinely used in each of the above preparations. Examples of the additives include excipients, binders, lubricants, disintegrators, emulsifiers, surfactants, bases, solubilizing adjuvants, and suspension agents.

Examples of the excipient include lactose, sucrose, starch, and dextrin. Examples of the binder include polyvinyl alcohol, gum arabic, tragacanth, gelatin, hydroxypropylmethylcellulose, hydroxypropylcellulose, sodium carboxymethylcellulose, and polyvinyl pyrrolidone. Examples of the lubricant include magnesium stearate, calcium stearate, and talc. Examples of the disintegrator include crystalline cellulose, agar, gelatin, calcium carbonate, sodium bicarbonate, and dextrin. Examples of the emulsifier or surfactant include Tween 60, Tween 80, Span 80, and glyceryl monostearate. Examples of the base include cetostearyl alcohol, lanolin, polyethylene glycol, rice bran oil, fish oil (DHA, EPA, etc.), and olive oil. Examples of the solubilizing adjuvants include polyethylene glycol, propylene glycol, sodium carbonate, sodium citrate, and Tween 80. Examples of the suspension agent include Tween 60, Tween 80, Span 80, glyceryl monostearate, polyvinyl alcohol, polyvinyl pyrrolidone, methylcellulose, hydroxymethylcellulose, and sodium alginate.

The intestinal tract protective agent of the present invention may be used as a pharmaceutical product component, food or beverage component, food or beverage additive, feed component, feed additive, etc.

The intestinal tract protective agent of the present invention may be used, for example, as an additive for foods or beverages such as water, soft drinks, fruit juice drinks, milk beverages, alcoholic beverages, breads, noodles, rice, tofu, dairy products, shoyu, miso, snacks, etc. These foods or beverages may further contain other additives commonly used in this field and examples include bittering agents, flavors, apple fiber, soybean fiber, meat extracts, black vinegar extract, gelatin, cornstarch, honey, animal fats and vegetable oils; monosaccharides such as glucose, fructose, etc.; disaccharides such as sucrose, etc.; polysaccharides such as dextrose, starches, etc.; sugar alcohols such as erythritol, xylitol, sorbitol, mannitol, etc.; vitamins such as vitamin C, etc.

The intestinal tract protective agent of the present invention may also be used as a component for foods for specified health uses, foods for specified dietary use, supplements, health food products, functional food products, food products for the sick, etc.

The intestinal tract protective agent of the present invention may be administered to a human or may be administered to a non-human mammal. The dose and administration route may be suitably determined in accordance with the conditions, age, etc., of an individual to be administered. Examples of the preferred administration route include oral administration, suppository administration and rectal administration.

Another embodiment of the present invention provides a microorganism, which produces the above polyphosphoric acid used to suppress the decline of intestinal tract barrier function or to recover the intestinal tract barrier function or used as a prophylactic or ameliorating agent for inflammatory bowel diseases.

The microorganism which produces the above polyphosphoric acid may be obtained by screening for the polyphosphoric acid productivity as the indicator. The screening method using the polyphosphoric acid productivity as the indicator may be carried out, for example, by culturing test microorganisms under culture conditions (medium composition, culture temperature, etc.) suitable for each strain, measuring an amount of the polyphosphoric acid produced in the culture supernatant after the culture and obtaining the strain produced a large amount of the polyphosphoric acid. The measurement of the amount of the polyphosphoric acid in the culture supernatant may be carried out by directly measuring an amount of the polyphosphoric acid using toluidine blue O (TBO) method or may be carried out in combination with the measurement of the amount of the polyphosphoric acid by molybdenum blue method. Alternatively, the culture supernatant is analyzed by HPLC or the like, to analyze an amount of the polyphosphoric acid present and a molecular weight of the polyphosphoric acid, whereby the strain which produces the polyphosphoric acid having an intended molecular weight may be selected.

The microorganism according to the present embodiment produces the above polyphosphoric acid and hence may be used to suppress the decline of intestinal tract barrier function or to recover the intestinal tract barrier function, or to prevent or ameliorate inflammatory bowel diseases. The above microorganism may be used as viable cells or may be used in the fragmented form.

The microorganism according to the present embodiment may also be used, as in the above intestinal tract protective agent, as a pharmaceutical product component, food or beverage component, food or beverage additive, feed component, feed additives, etc., and as a component for foods for specified health uses, foods for specified dietary use, supplements, health food products, functional food products, food products for the sick, etc.

Examples of the microorganism according to the present embodiment include *Lactobacillus rhamnosus* GG strain, *Lactobacillus brevis* SBC8803 strain, strains belonging to genera *Lactobacillus, Bifidobacterium, Enterococcus, Lactococcus, Pediococcus, Leuconostoc, Streptococcus, Bacteroidetes, Eubacterium*, and *Clostridium*.

It is preferred that the above microorganism according to the present embodiment be a lactic acid bacterium. Since lactic acid bacteria can survive in the intestines, when used as viable cells, continuous supply of the above polyphosphoric acid can be achieved, rendering higher effects. It is preferred that the above lactic acid bacterium be *Lactobacillus brevis* SBC8803 strain. *Lactobacillus brevis* is a member of lactic acid bacteria which has been used in the fermented food products since ancient times and the safety thereof to the living body has been established. For this reason, *Lactobacillus brevis* can be consumed continuously for an extended period of time, whereby it is feasible to more effectively suppress the decline of intestinal tract barrier function or to recover the intestinal tract barrier function, or to prevent or ameliorate inflammatory bowel diseases.

EXAMPLES

Example 1

Expression Induction of HSP 27 by Culture Supernatant of *Lactobacillus brevis* SBC8803 Strain Using human colon cancer-derived intestinal tract epithelium cell (Caco-2/bbe cell), the expression induction of HSP 27 by the culture supernatant of a lactic acid bacterium, *Lactobacillus brevis* SBC8803 strain was analyzed.

(Preparation of Culture Supernatant)

*Lactobacillus brevis* SBC8803 strain was cultured in DeMan-Rogosa-Sharpe (MRS) medium (made by Difco Laboratories) for 24 hours at 37° C. in an incubator to obtain the culture supernatant. Further, unused MRS medium was prepared as a control. Next, the culture time was changed to 12 hours, 36 hours and 60 hours to obtain the culture supernatants in the same manner. The $OD_{600}$ values of the culture broth when cultured for 12 hours, 36 hours and 60 hours were 0.069, 0.443 and 0.398, respectively. These values, on a basis of lactic acid bacterium count, were $0.11 \times 10^9$, $1.07 \times 10^9$, $0.95 \times 10^9$ cfu/ml, respectively.

(Culture of Caco-2/Bbe Cell)

The Caco-2/bbe cell was obtained from ATCC (catalog No. CRL-2102). Caco-2/bbe cells were cultured in high glucose Dulbecco's Modified Eagle Medium (DMEM) supplemented with 10% (v/v) fetal calf serum (FBS), 2 mM L-glutamine, 50 U/ml penicillin, 50 μg/ml streptomycin and 10 μg/ml transferrin (all reagents are made by Invitrogen/GIBCO) using a $CO_2$ incubator at 37° C. under 5% $CO_2$ atmosphere. The Caco-2/bbe cells maintained and subcultured under the above conditions were inoculated in a 6-well or 12-well culture plate to have a density of $10^5$ cells/$cm^2$ and cultured for 10 to 14 days until differentiated. In each test, the thus differentiated Caco-2/bbe cell was used.

(Induction of HSP 27 Protein by the Culture Supernatant)

Caco-2/bbe cell was cultured in medium containing 10% (v/v) of the culture supernatant of Lactobacillus brevis SBC8803 strain for 24 hours and the expression amount of HSP 27 protein was analyzed by the western blot method.

(Analysis by Western Blot Method)

The analysis of the protein by the western blot method was carried out as follows.

The protein was extracted from Caco-2/bbe cells washed with phosphate buffered saline (PBS) using a Mammalian Cell Extraction kit (made by BioVision Incorporated). 10 to 30 μg of the extracted protein was fractionated by SDS-PAGE and immediately transferred onto a nitrocellulose membrane in a transfer buffer (25 mM Tris, pH 8.8, 192 mM glycine, 20% v/v methanol).

The nitrocellulose membrane after the transfer (blot) was incubated in T-PBS (PBS containing 0.05% v/v of Tween 20) containing 5% (v/v) skim milk or 1% (v/v) bovine serum albumin (made by Sigma-Aldrich Corp.) at room temperature for 1 hour and the blot was blocked. Subsequently, using anti-HSP 27 antibody and anti-HSC 70 antibody (both are made by Stressgen) as the primary antibodies, the blot was incubated overnight at 4° C. After incubation, the blot was washed for 10 minutes at room temperature using T-PBS. The washing was repeated three times and the blot was incubated with a secondary antibody for 60 minutes. As the secondary antibody, an HRP labeled antibody (made by R&D Systems, Inc.) suitable for the organism from which the primary antibodies are derived was used. After washing the blot three times with T-PBS, signals were detected by a chemiluminescence method using a Super-Signal West Pico enhanced chemiluminescence system (made by Pierce Chemical Company).

The results of the western blot are shown in FIG. 1. HSC 70 is constitutively-expressed protein and used herein as the loading control. Caco-2/bbe cells were cultured for 24 hours in medium containing 10% (v/v) of unused MRS medium (control) or in medium containing 10% (v/v) of the culture supernatant of which Lactobacillus brevis SBC8803 was cultured for 24 hours (culture supernatant containing medium), and the western blot analysis was carried out. The expression amount of HSC 70 was not significantly different under both conditions, whereas the expression amount of HSP 27 was significantly high when cultured in the culture supernatant containing medium (FIG. 1(A)). Further, the culture supernatant of which Lactobacillus brevis SBC8803 strain was cultured for 12 hours induced the expression of HSP 27 more intensely than the culture supernatants of which the microorganism was cultured for 36 hours and 60 hours (FIG. 1(B)).

From the above results, it was revealed that the expression of HSP 27 is induced in the human colon cancer-derived intestinal epithelium cell Caco-2/bbe cells by the culture supernatant of Lactobacillus brevis SBC8803 strain. Also, it was found that the expression amount of HSP 27 induced by this culture supernatant depends on the time during which Lactobacillus brevis SBC8803 strain was cultured when preparing the culture supernatant.

Example 2

Separation of HSP 27 Expression Inducing Substance

Since it was revealed that the expression of HSP 27 can be induced by the culture supernatant of Lactobacillus brevis SBC8803 strain, the separation of HSP 27 expression inducing substance was subsequently undertaken.

(Separation of HSP 27 Expression Inducing Substance Using an MWCO Membrane)

The culture broth of Lactobacillus brevis SBC8803 strain was subjected to centrifugal separation for 10 minutes at a centrifugal acceleration of 500×g, the culture supernatant was collected and filtered using a filter having a pore size of 0.2 μm to obtain the filtrate. The components contained in the obtained filtrate were fractionated using a Vivaspin ultrafiltration spin column (made by Vivascience) equipped with an MWCO membrane with a molecular weight cut off (MWCO) of 5 kDa, 10 kDa, 30 kDa or 50 kDa. Next, the expression induction of HSP 27 by the permeate passed through the MWCO membrane was analyzed in the same manner as in Example 1.

(Separation of HSP 27 Expression Inducing Substance by Ammonium Sulfate Precipitation)

The culture broth of Lactobacillus brevis SBC8803 strain was subjected to centrifugal separation for 10 minutes at a centrifugal acceleration of 500×g, the culture supernatant was collected and filtered using a filter having a pore size of 0.2 μm to obtain the filtrate. Ammonium sulfate was added to the obtained filtrate with stirring until 65% saturation was obtained. At the 65% saturation, the filtrate was subjected to centrifugal separation for 10 minutes at a centrifugal acceleration of 5000×g to fractionate the precipitation (65% ammonium sulfate pellet) and the supernatant. Ammonium sulfate was further added thereto with stirring until 90% saturation with respect to the fractionated supernatant was obtained. At the 90% saturation, the supernatant was subjected to centrifugal separation for 10 minutes at a centrifugal acceleration of 5000×g to fractionate the precipitation (90% ammonium sulfate pellet) and the supernatant (ammonium sulfate supernatant). The precipitation (65% ammonium sulfate pellet and 90% ammonium sulfate pellet) was dissolved in distilled water and desalted using a dialysis tube with a molecular weight cut off of 7000 (made by Pierce Chemical Company). The expression inductions of HSP 27 by the thus obtained aqueous solution of 65% ammonium sulfate pellet, the aqueous solution of 90% ammonium sulfate pellet and the ammonium sulfate supernatant were analyzed in the same manner as in Example 1.

The results of western blot are shown in FIG. 2. HSC 70 was used as the loading control as in Example 1.

Caco-2/bbe cell was cultured for 24 hours in medium containing 10% (v/v) of unused MRS medium (control), medium containing 10% (v/v) of the culture supernatant which was not fractionated by an MWCO membrane (culture supernatant) and medium containing 10% (v/v) of the permeate passed through an MWCO membrane of 5 kDa, 10 kDa, 30 kDa or 50 kDa (5 kDa MWCO membrane permeate, 10 kDa MWCO membrane permeate, 30 kDa MWCO membrane permeate and 50 kDa MWCO membrane permeate, respectively) and the western blot analysis was carried out. As a result, the 5 kDa MWCO membrane permeate and the 10 kDa MWCO membrane permeate had about the same HSP 27 expression amount as the control (FIG. 2(A)). On the other hand, the 30 kDa MWCO membrane permeate and the 50 kDa MWCO membrane permeate had about the same HSP 27 expression amount as the culture supernatant (FIG. 2(A)).

Caco-2/bbe cell was cultured for 24 hours in medium containing 10% (v/v) of the aqueous solution of 65% ammonium sulfate pellet, the aqueous solution of 90% ammonium sulfate pellet and the ammonium sulfate supernatant, respectively in the form of a 100 fold diluted solution (1/100), a 10 fold diluted solution (1/10) and a 1 fold diluted solution (1) the western blot analysis was carried out. As a result, the expression of HSP 27 was intensely induced by the aqueous solution of 65% ammonium sulfate pellet (FIG. 2(B)).

From the results of Example 2, it was revealed that the HSP 27 expression inducing substance is mainly contained in the components which do not pass through a 10 kDa MWCO membrane and is mainly contained in the 65% ammonium sulfate pellet.

Example 3

Isolation of HSP 27 Expression Inducing Substance

The HSP 27 expression inducing substance was isolated from the 65% ammonium sulfate pellet of Example 2.

(Anion-Exchange Chromatography Separation)

An aqueous solution of the 65% ammonium sulfate pellet was added to a column filled with DEAE Sephadex A-50 (made by GE Healthcare). Next, 0 M, 0.1 M, 0.5 M and 1 M NaCl solutions prepared with 20 mM Tris-HCl (pH 8.5) were added in this order to the column, from which the adsorbed components were eluted. The expression induction of HSP 27 by each eluate was analyzed in the same manner as in Example 1.

(Size Exclusion Chromatography Separation)

The fraction eluted from the 1.0 M NaCl by the anion-exchange chromatography was loaded into the column filled with Sephadex G-100 and eluted with 20 mM phosphate buffer (pH 6.5). The eluate was collected in 5 ml per fraction in 20 divided fractions. The expression induction of HSP 27 by each eluate of the obtained 20 fractions was analyzed in the same manner as in Example 1.

(HPLC Separation)

Using a Shodex KW800 column (300 mm×8 mm, made by Showa Denko K.K.), the eluates collected as Fraction Nos. 17 and 18 in the size exclusion chromatography were further fractionated by AKTA design HPLC system (made by GE Healthcare). Using 20 mM phosphate buffer (pH 6.5) as the eluate, samples were eluted at a flow rate of 0.1 ml/min. The eluted liquids were monitored by the absorption of UV light at a wavelength of 220 nm and elution fractions at which absorption peaks (A1 to A3) were found were fractionated. The expression inductions of HSP 27 by the fractionated elution fractions were analyzed in the same manner as in Example 1.

The analysis results of the isolation state at each process in the isolation of the HSP 27 expression inducing substance are shown in FIG. 3. The expression inductions of HSP 27 by the 0 M NaCl eluate, 0.1 M NaCl eluate, 0.5 M NaCl eluate and 1.0 M NaCl eluate obtained by the anion-exchange chromatography separation were analyzed by the western blot. As a result, the expression of HSP 27 was induced intensely by the 1.0 M NaCl eluate (FIG. 3(A)).

The expression inductions of HSP 27 by the eluates separated by the size exclusion chromatography were analyzed by the western blot. The eluates were numbered with fraction numbers 1 to 20 in the order of being eluted. As the results of western blot, the expression induction of HSP 27 was observed by the eluates in Fraction Nos. 14 to 19 and the expression was induced intensely in the eluates in Fraction Nos. 17 and 18 in particular (FIG. 3(B)).

FIG. 4(A) shows an HPLC chart. In the chart, the axis of abscissa indicates the retention time and the axis of ordinate indicates the absorbance at a wavelength of 220 nm. Under the above HPLC conditions, three major peaks (A1 to A3) were observed (FIG. 4(A)). The elution fractions corresponding to A1 to A3 peaks were fractionated and the expression inductions of HSP 27 were analyzed by the western blot. The results are shown in FIG. 4(B). The graphs in FIG. 4(B) show the results of calculated percentage of HSP 27 protein amount with respect to HSC 70 by measuring the HSC 70 and HSP 27 protein amounts from the western blot results (FIG. 4(B)). The concentrations (μg/ml) shown in FIG. 4(B) are those determined from the absorbance at 220 nm, assuming that the component contained in each elution fraction is a protein. As the results of western blot, the expression of HSP 27 protein was induced in a dose-dependent manner by the A1 fraction and A2 fraction (FIG. 4(B)).

From the above results, it was revealed that the HSP 27 expression inducing substance is predominantly present in the A1 fraction and A2 fraction obtained by HPLC as the results of purifying the culture broth of *Lactobacillus brevis* SBC8803 strain by ammonium sulfate precipitation, anion-exchange chromatography, size exclusion chromatography and HPLC.

Example 4

Identification of HSP 27 Expression Inducing Substance

Using the A1 fraction and A2 fraction obtained in Example 3, the identification of HSP 27 expression inducing substance was carried out. First, the A1 fraction and A2 fraction were subjected to the conditions under which an acid hydrolysis reaction of a protein takes place, whereby the amino acid composition contained in the A1 fraction and A2 fraction was analyzed. However, amino acid components were not detected in the A1 fraction or A2 fraction (data not shown). Also, the contents of neutral sugar and uronic acid were lower than 1% (data not shown). More specifically, the HSP 27 expression inducing substance was not a protein or a polysaccharide. Next, the A1 fraction and A2 fraction were subjected to the elementary analysis using an electron microscope scanning and the results showed that these fractions contain a large amount of phosphorus and oxygen (data not shown). Then, the measurements of the polyphosphoric acid and phosphoric acid contents were carried out by toluidine blue O (TBO) method and molybdenum blue method.

(Measurement of Amount of Polyphosphoric Acid by the TBO Method)

The measurements of the amount of polyphosphoric acid in the A1 fraction and A2 fraction were carried out by the TBO method. Using the A1 fraction and A2 fraction as the samples, 10 µl of each was mixed with 500 µl of a TBO assay solution. The TBO assay solution is that in which TBO is dissolved in 0.1N acetic acid so as to give a concentration of 15 mg/ml. After allowing the reaction to proceed for 15 minutes at room temperature, an absorbance at a wavelength of 620 nm was immediately measured.

(Measurement of Amount of Phosphoric Acid by the Molybdenum Blue Method)

An equal amount of 2 N hydrochloric acid was added to 5 µl each of the A1 fraction and A2 fraction which was then incubated for 30 minutes at 95° C. to acid hydrolyze the polyphosphoric acid. Using the thus obtained acid hydrolyzed solutions as the samples, the amount of phosphoric acid was measured by the molybdenum blue method. Sterilized water was added to the acid hydrolyzed solution to give 300 µl and 700 µl of the molybdenum blue assay solution was added and mixed. The molybdenum blue assay solution is the solution in which $(NH_4)6Mo_7O_{24} \cdot 4H_2O$ is dissolved in a solvent of 1 N sulfuric acid and 10% (w/v) ascorbic acid mixed in a 6:1 ratio so as to give 0.42 (w/v) %. After allowing the mixed solution to react at 45° C. for 20 minutes, an absorbance at a wavelength of 750 nm was measured and a phosphoric acid concentration was calculated from the standard curve produced using a phosphoric acid solution with a known concentration.

Table 1 shows the measurement results of the amount of polyphosphoric acid by the TBO method. Compared with the blank, in the samples of A1 fraction and A2 fraction, the absorbances at a wavelength of 620 nm were reduced. This is caused by the metachromasia in TBO and indicates the presence of polyphosphoric acid in the A1 faction and A2 faction.

TABLE 1

Measurement results of amount of polyphosphoric acid by TBO method

|  | Absorbance (620 nm) | Polyphosphoric acid concentration (mg/ml) |
|---|---|---|
| A1 Fraction | 1.522 | 1.48 |
| A2 Fraction | 1.489 | 1.75 |
| Blank | 1.586 |  |

Table 2 shows the measurement results of the amount of polyphosphoric acid by the molybdenum blue method. Both fractions contained 60% or more of phosphoric acid.

TABLE 2

Measurement results of amount of phosphoric acid by molybdenum blue method

|  | Standard solution phosphoric acid concentration (mg/ml) | Absorbance (750 nm) | Phosphoric acid concentration (Calculated value) (mg/ml) |
|---|---|---|---|
| A1 Fraction |  | 0.029 | 0.788 |
| A2 Fraction |  | 0.034 | 0.924 |
| Standard | 10.00 | 0.345 |  |
| phosphoric | 5.00 | 0.225 |  |
| acid | 2.50 | 0.092 |  |
| solution | 1.25 | 0.063 |  |
|  | 0.63 | 0.032 |  |
| Blank | 0.00 | 0.001 |  |

From the above results, it was strongly suggested that the HSP 27 expression inducing substance present in the culture supernatant of *Lactobacillus brevis* SBC8803 strain is polyphosphoric acid. The above A2 fraction was termed as LPP (*Lactobacillus brevis*-derived polyphosphate).

Example 5

Verification of HSP 27 Expression Induction by Polyphosphoric Acid

Polyphosphoric acid in LPP was decomposed by a catabolic enzyme to analyze whether the HSP 27 expression induction ability by LPP was lost.

(Polyphosphoric Acid Decomposition in LPP)

2 µl of LPP was reacted in a reaction solution having the total volume of 30 µl at 37° C. for 3 hours to decompose polyphosphoric acid. The reaction solution was composed of 50 mmol/L ammonium sulfate, 4 mmol/L $MgCl_2$, 10 µmon ADP, 40 mmol/L HEPES-KOH (pH 7.5) and 1 U/µl *Propionibacterium shermanii*-derived polyphosphoric acid kinase (PPK). After reaction, the reaction solution was incubated at 95° C. for 2 minutes to deactivate PPK, thereby obtaining LPP in which polyphosphoric acid was decomposed. The expression induction of HSP 27 by the polyphosphoric acid-decomposed LPP was analyzed in the same manner as in Example 1. The enzymatic reaction caused by PKK is reversible but, when a larger amount of ADP is present than ATP in the reaction solution, the decomposition reaction of polyphosphoric acid prevails so that an ADP/ATP ratio reaches equilibrium. Consequently, under the above reaction conditions, the reaction proceeds in the direction of decomposing polyphosphoric acid.

Figure 5:
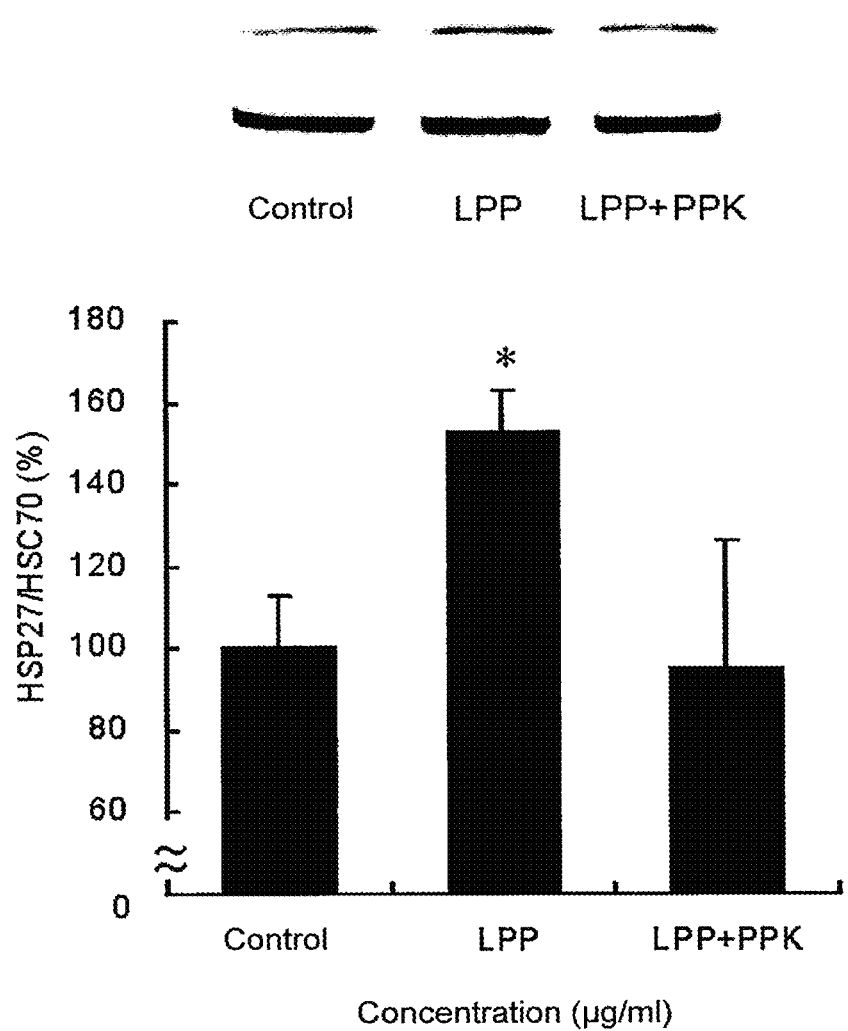
FIG. 5 is pictures of western blot showing the analysis results of HSP 27 expression induction by a divided polyphosphoric acid in Example 5.

FIG. 5 shows the analysis results of the HSP 27 expression induction by polyphosphoric acid-decomposed LPP by the western blot. The graphs in FIG. 5 show the results of calculated percentage of HSP 27 protein amount with respect to HSC 70 by measuring the HSC 70 and HSP 27 protein amounts from the western blot results when the control is 100% (FIG. 5). In FIG. 5, a label LPP refers to the LPP in which the decomposition reaction of polyphosphoric acid was not carried out and LPP+PPK refers to the LPP in which polyphosphoric acid was decomposed. As evident in FIG. 5, the expression of HSP 27 was not induced by the decomposition of polyphosphoric acid in LPP.

From the above results, it was revealed that the HSP 27 expression by LPP is not induced when polyphosphoric acid is decomposed by causing a polyphosphoric acid catabolic enzyme to act on LPP in the presence of excess ADP. Consequently, it was revealed that the HSP 27 expression inducing substance is polyphosphoric acid.

Example 6

Improvement in the Intestinal Tract Disorder and Survival Rate by LPP in DSS-Treated Mouse Using mice in which an intestinal tract (intestinal mucosa) disorder was induced by administering a median lethal dose of dextran sulfate sodium (DSS), the effects of polyphosphoric acid (LPP) on the intestinal tract disorder and survival rate were analyzed.

(Analysis on the Survival Rate in Mouse Treated with a Median Lethal Dose of DSS)

A C57Bl/6 mouse was given drinking water to which DSS (molecular weight 2,500) was added so as to attain 4% (w/v). Subsequently, 10 µg of LPP dissolved in 100 µl of PBS was transrectally administered every day to LPP group (n=5) to be tested during the test period. On the other hand, 100 µl of PBS was transrectally administered every day to Control group (n=5) as a comparison during the test period.

For 20 days from the start of test, the survival state of the test mouse was monitored and the survival curve was determined.

(Analysis on the Intestinal Tract Disorder in DSS-Treated Mouse)

A C57Bl/6 mouse was given drinking water to which DSS was added so as to attain 3% (w/v). Subsequently, 10 µg of LPP dissolved in 100 µl of PBS was transrectally administered every day to LPP group (n=5) to be tested during the test period. On the other hand, 100 µl of PBS was transrectally administered every day to Control group (n=5) as a comparison during the test period. On day 7 from the start of test, the entire colon from the cecum to the anus was removed from the mouse and the colon length was measured.

(Histological Analysis)

The colon was immobilized in a 10% buffer formalin solution and paraffin-embedded by a routine method. The paraffin-embedded colon was cut into pieces sized 5 µm and stained with hematoxylin-eosine (HE) to observe using an optical microscope.

Figure 6:
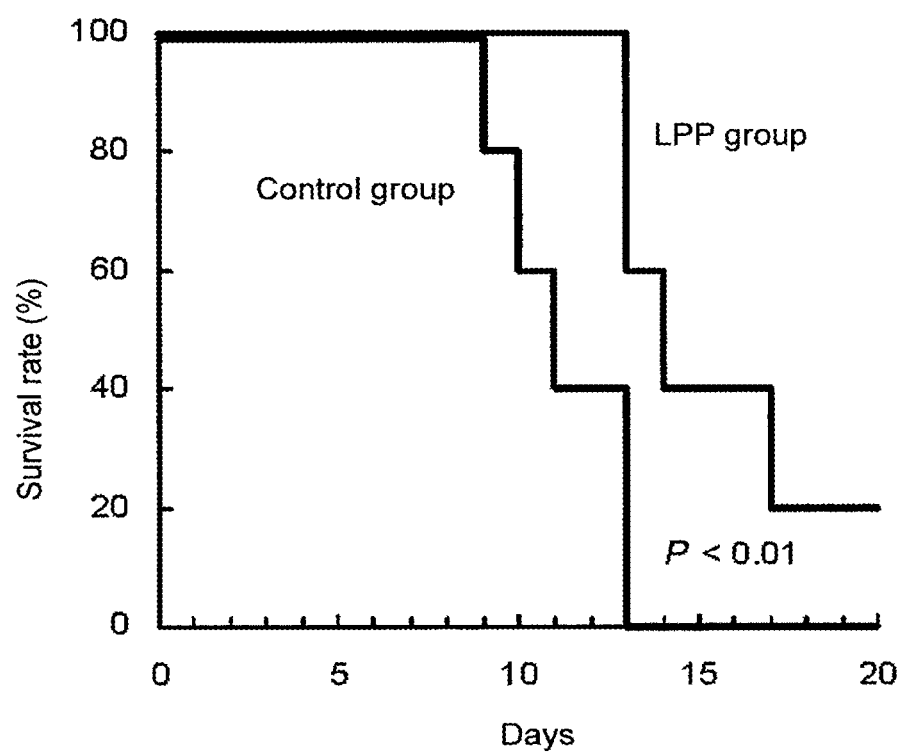
FIG. 6 is a survival curve of acute enteritis-induced mice in Example 6.

FIG. 6 shows the survival curve. In Control group, all mice died within 13 days from the start of test, whereas in LPP group 60% of the mice survived on day 13 (FIG. 6). The cumulative survival rate of LPP group was significantly higher than the cumulative survival rate of Control group.

Figure 7:
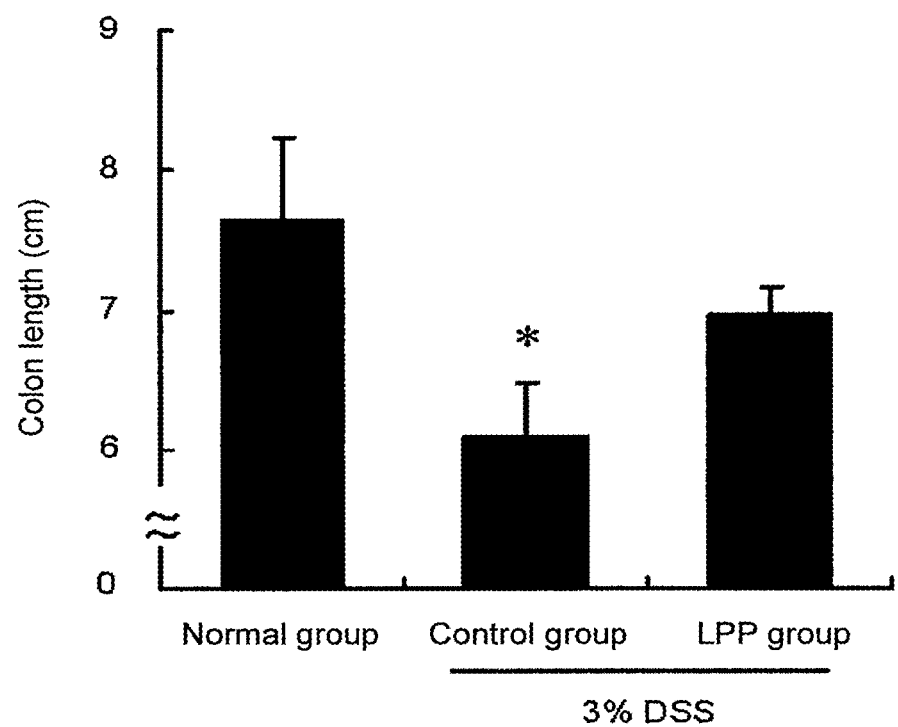
FIG. 7 is a graph showing the colon length of the acute enteritis-induced mice in Example 6.

FIG. 7 shows the measurement results of colon length. The colon length of LPP group had no significant difference in comparison with the colon length of normal mice which were not treated with DSS. On the other hand, the colon length of Control group was significantly shorter than the colon length of normal mice (FIG. 7). This result indicates that the intestinal tract disorder induced by the DSS treatment was suppressed or ameliorated by the LPP administration.

Figure 8:
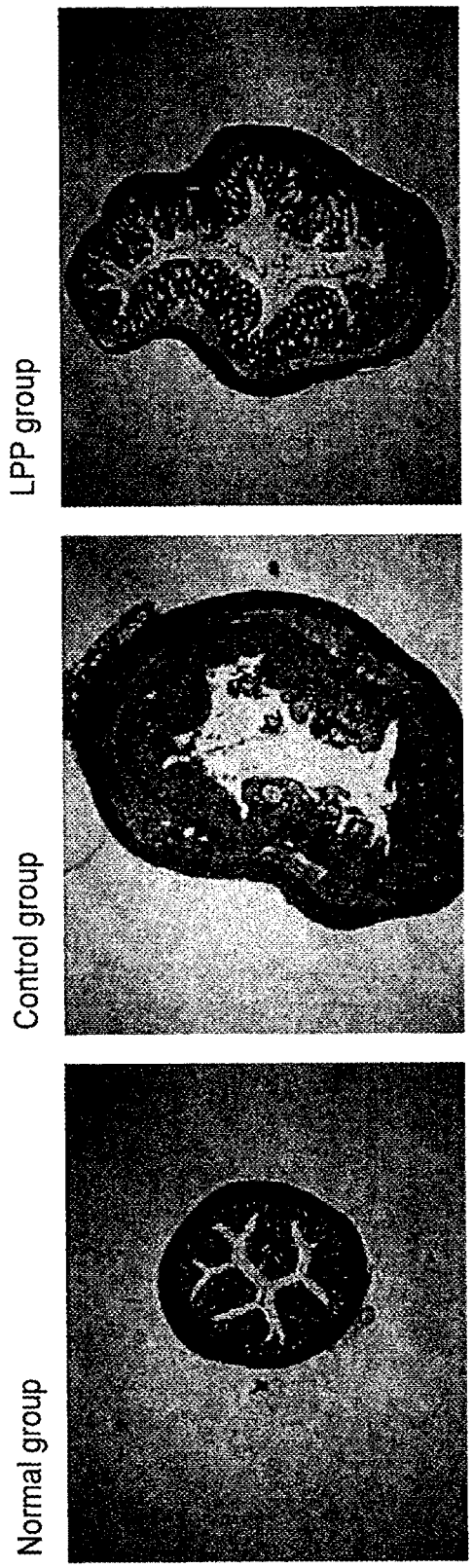
FIG. 8 is pictures of stained intestinal tissues of acute enteritis-induced mice in Example 6.

Pictures of typical HE-stained colon samples are shown in FIG. 8. Compared with Control group, the amelioration of intestinal tract disorder was observed in LPP group.

As the result of Example 6, it was revealed that the LPP administration can enhance the survival rate in the mouse treated with a median lethal dose of DSS and suppress or ameliorate the intestinal tract disorder.

Example 7

Expression Induction of HSP 27 by Enzymatically Synthesized Polyphosphoric Acid

The expression induction of HSP 27 by polyphosphoric acid enzymatically synthesized in vitro (enzymatically synthesized polyphosphoric acid) was analyzed.

(Synthesis of Polyphosphoric Acid)

1 ml of a reaction solution containing 50 mM Tris-HCl (pH 7.4), 40 mM ammonium sulfate, 4 mM $MgCl_2$, 40 mM creatine phosphate, 20 ng/ml creatine kinase, 1 mM ATP (pH 7.2) and 1 U/ml PPK was reacted at 37° C. for 3 hours. After reaction, 100 µl of 50 mM $CaCl_2$ was added to the reaction solution to aggregate the synthesized polyphosphoric acid. Then, the reaction solution was subjected to centrifugal separation for 10 minutes at a centrifugal acceleration of 5,000×g to collect the precipitate of polyphosphoric acid. The precipitate was dissolved in a 50 mM EDTA solution and dialyzed using a dialysis membrane with a molecular weight cut off of 3,000 to obtain a polyphosphoric acid purified solution from which low weight molecules such as Ca ion and EDTA were removed. Next, the polyphosphoric acid purified solution was further fractionated in the same manner as in Example 3 by HPLC using a Shodex KW800 column. The eluted liquid was monitored by the ultraviolet light absorption at a wavelength of 220 nm and the elution fractions corresponding to the major peaks appeared at about 10 minute retention time were fractionated. The expression inductions of HSP 27 by the fractionated elution fractions were analyzed in the same manner as in Example 1.

Figure 9:
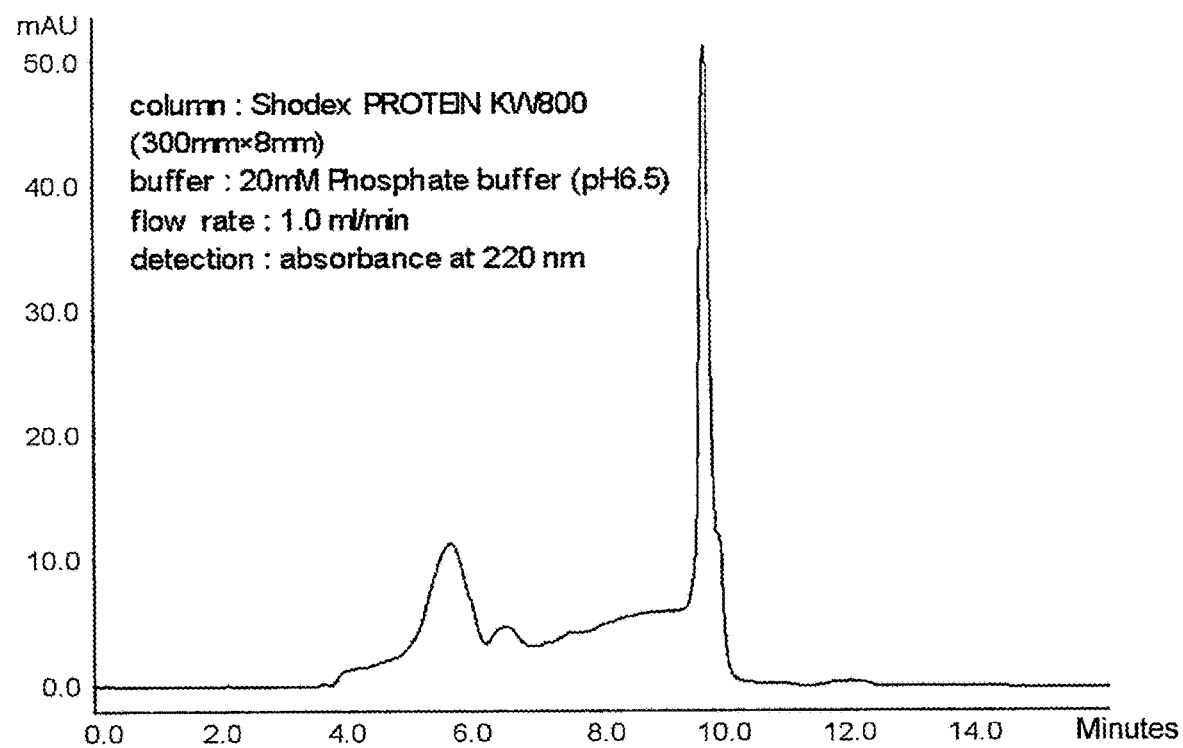
FIG. 9 is an HPLC chart of synthetic polyphosphoric acid in Example 7.

The HPLC chart of polyphosphoric acid purified solution is shown in FIG. 9. The axis of abscissa of chart is the retention time (minute) and the axis of ordinate is the absorbance at a wavelength of 220 nm. As shown in FIG. 9, a major peak appeared at about 10 minute retention time. The elution fraction corresponding to the peak was fractionated to be the enzymatically synthesized polyphosphoric acid. Since the enzymatically synthesized polyphosphoric acid has a faster elution rate than LPP in size exclusion chromatography, it was believed to have higher molecular weight than LPP.

Figure 10:
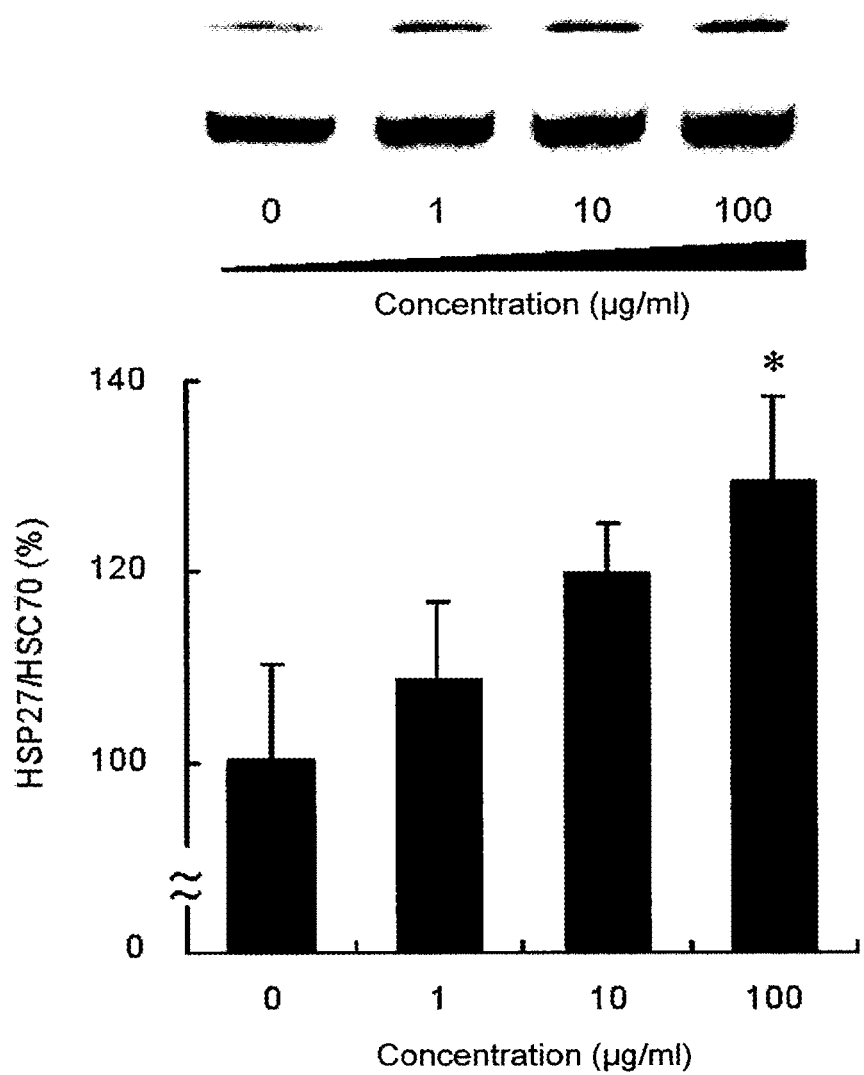
FIG. 10 is pictures of western blot showing HSP 27 expression induction by synthetic polyphosphoric acid in Example 7.

The analysis results of HSP 27 expression induction by the enzymatically synthesized polyphosphoric acid by the western blot are shown in FIG. 10. The graph shown in FIG. 10 was produced in the same manner as in the graph of FIG. 5. As evident in FIG. 10, the expression of HSP 27 was induced in a dose-dependent manner by the enzymatically synthesized polyphosphoric acid.

From the above results, it was revealed that the expression of HSP 27 is induced by the polyphosphoric acid synthesized enzymatically in vitro (enzymatically synthesized polyphosphoric acid), in addition to the polyphosphoric acid contained in LPP.

Example 8

Improvement in the Intestinal Tract Disorder and Survival Rate by Polyphosphoric Acid in DSS-Treated Mouse Using a mouse in which an intestinal tract (intestinal mucosa) disorder was induced by administering a median lethal dose of dextran sulfate sodium (DSS), the effects of polyphosphoric acid on the intestinal tract disorder and survival rate were analyzed. As the polyphosphoric acid, the enzymatically synthesized polyphosphoric acid, which was enzymatically synthesized by the method described in Example 7 was used.

(Analysis on the Survival Rate in Mouse Treated with a Median Lethal Dose of DSS)

A C57Bl/6 mouse was given drinking water to which DSS (molecular weight 2,500) was added so as to attain 5% (w/v). Subsequently, 1 µg of the enzymatically synthesized polyphosphoric acid dissolved in 100 µl of PBS was transrectally administered every day to 1 µg polyphosphoric acid group (n=5) to be tested during the test period. 10 µg of the enzymatically synthesized polyphosphoric acid dissolved in 100 µl of PBS was transrectally administered every day to 10 µg polyphosphoric acid group (n=5) during the test period. On the other hand, 100 µl of PBS was transrectally administered every day to Control group (n=5) as a comparison during the test period. For 15 days from the start of test, the survival state of the test mouse was monitored and the survival curve was determined.

(Analysis on the Intestinal Tract Disorder in DSS-Treated Mouse)

A C57Bl/6 mouse was given drinking water to which DSS was added so as to attain 5% (w/v). Subsequently, 1 µg of the enzymatically synthesized polyphosphoric acid dissolved in 100 µl of PBS was transrectally administered every day to 1 µg polyphosphoric acid group (n=5) to be tested during the test period. 10 µg of the enzymatically synthesized polyphosphoric acid dissolved in 100 µl of PBS was transrectally administered every day to 10 μg polyphosphoric acid group (n=5) during the test period. On the other hand, 100 μl of PBS was transrectally administered every day to Control group (n=5) as a comparison during the test period. On day 7 from the start of test, the entire colon from the cecum to the anus was removed from the mouse and the colon length was measured.

Figure 11:
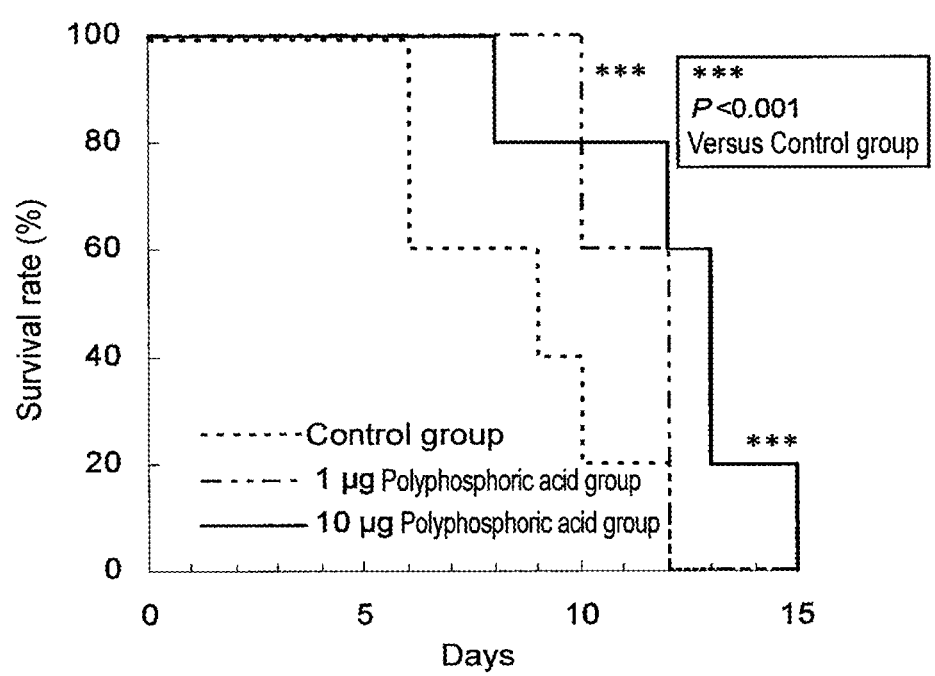
FIG. 11 is a survival curve of acute enteritis-induced mice in Example 8.

FIG. 11 shows the survival curve. In Control group, all mice died within 12 days from the start of test, whereas in 10 μg polyphosphoric acid group 60% of the mice survived on day 12 (FIG. 11). The cumulative survival rates of 1 μg polyphosphoric acid group and 10 μg polyphosphoric acid group were significantly higher than the cumulative survival rate of Control group.

Figure 12:
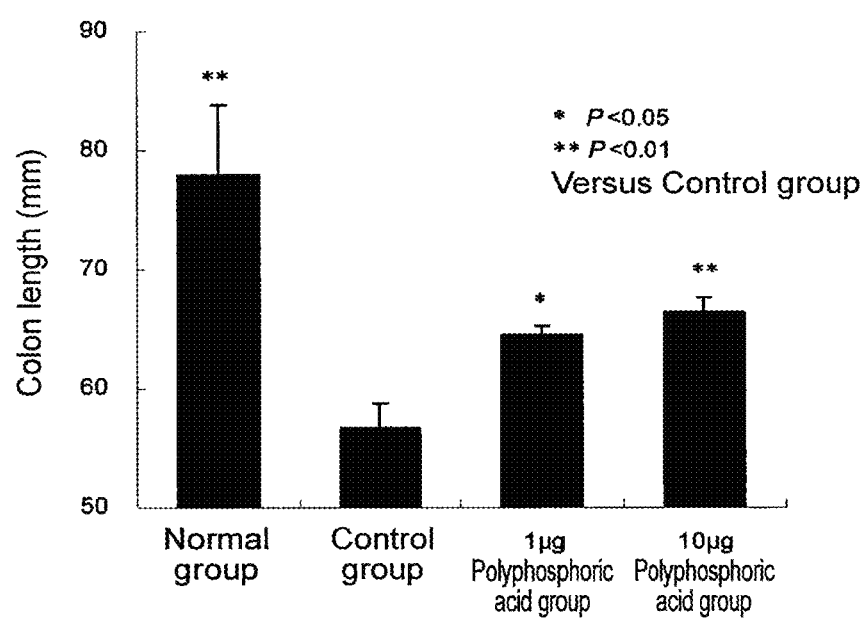
FIG. 12 is a graph showing the colon length of acute enteritis-induced mice in Example 8.

The measurement results of colon length are shown in FIG. 12. The colon lengths of 1 μg polyphosphoric acid group and 10 μg polyphosphoric acid group were significantly longer than the colon length of Control group (FIG. 12). This result indicates that the intestinal tract disorder induced by the DSS treatment was suppressed or ameliorated by the administration of enzymatically synthesized polyphosphoric acid.

As the result of Example 8, it was revealed that the enzymatically synthesized polyphosphoric acid administration can also enhance the survival rate in the mouse treated with a median lethal dose of DSS and suppress or ameliorate the intestinal tract disorder.

Example 9

Enhancement of the Intestinal Tract Barrier Function by the Enzymatically Synthesized Polyphosphoric Acid Mannitol is an intestinal tract non-permeable substance by nature but is permeable when the intestinal tract barrier function is declined, such as when the cell adhesion structure like tight junction, etc., breaks. Using such a property of mannitol, the intestinal tract permeability experiment on mannitol was carried out by the ex vivo loop assay and the intestinal tract barrier function was evaluated.

The small intestine was removed from a 6-week old C57Bl/6 mouse, the inside of intestinal tract was washed with PBS and the small intestine was equally divided into three. After ligating one end of the small intestine using a surgical suture, the respective small intestines were filled with PBS, a PBS solution containing 10 μg/ml of the enzymatically synthesized polyphosphoric acid and a PBS solution containing 100 μg/ml of the enzymatically synthesized polyphosphoric acid, and the other end was ligated in the same manner using a surgical suture. The enzymatically synthesized polyphosphoric acid used was that enzymatically synthesized by the method described in Example 7.

These small intestines were incubated in RPMI 1640 medium at 37° C. for 2 hours under 5% $CO_2$ atmosphere. After 2-hour incubation, the contents of the intestinal tract were removed and the intestinal tracts were further equally divided into two. Next, one of the intestinal tracts was filled with 1 μCi/ml of tritium-labeled mannitol dissolved in RPMI 1640 medium, and the other intestinal tract was filled with 1 μCi/ml of tritium-labeled mannitol dissolved in RPMI 1640 medium and 0.3 mM monochloramin ($NH_2Cl$) as an oxidizing agent.

After filling, the intestinal tracts were incubated in RPMI 1640 medium and the tritium amounts leaked out of the intestinal tract were measured 5 minutes, 20 minutes and 35 minutes later using a liquid scintillation counter. The value obtained by subtracting the value measured 5 minutes later from the value measured 20 minutes later represents the mannitol leakage of 15 minutes later, and similarly the value obtained by subtracting the value measured 5 minutes later from the value measured 35 minutes later represents the mannitol leakage of 30 minutes later.

Figure 13:
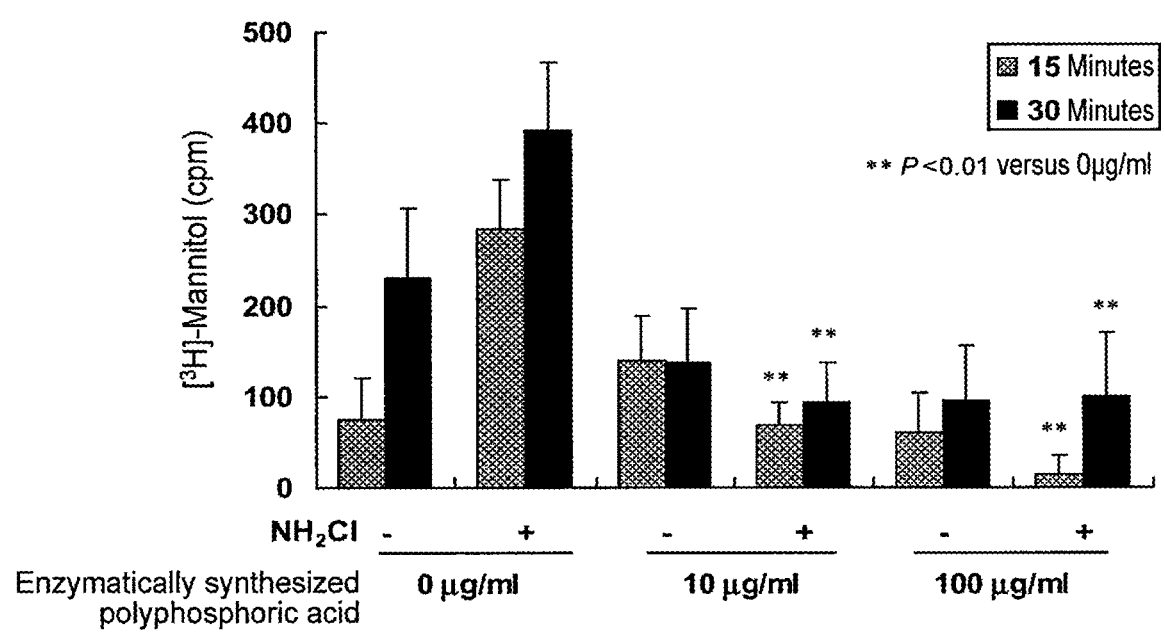
FIG. 13 is a graph showing the mannitol leakage in Example 9.

The graph of mannitol leakage is shown in FIG. 13. In the intestinal tract treated only with PBS, the mannitol leakage increased in a time-dependent manner, whereas in the intestinal tract treated with the enzymatically synthesized polyphosphoric acid, the time-dependent mannitol leakage increase was not found (FIG. 13). More specifically, it was indicated that the enzymatically synthesized polyphosphoric acid can suppress the decline of intestinal tract barrier function.

Further, when an oxidative stress was applied by monochloramin, the mannitol leakage increased several times in the intestinal tract treated only with PBS (FIG. 13), whereas the mannitol leakage decreased more in the intestinal tract treated with the enzymatically synthesized polyphosphoric acid than when the oxidative stress was not applied (FIG. 13). The results found in the intestinal tract treated only with PBS indicate that the intestinal tract barrier function is declined by the oxidative stress. Also, the results found in the intestinal tract treated with the enzymatically synthesized polyphosphoric acid indicate that polyphosphoric acid is capable of significantly suppressing the decline of the intestinal tract barrier function caused by the oxidative stress and recovering the intestinal tract barrier function.

As the result of Example 9, it was revealed that (the enzymatically synthesized) polyphosphoric acid recovers the intestinal tract barrier function and suppresses the decline of the intestinal tract barrier function.

Example 10

Suppression of Caspase Activation by Polyphosphoric Acid

Caspase-3 and caspase-9 are present in the form of inactive full-length caspase-3 and full-length caspase-9 and decomposed by the actions of other proteases (post-translational modification) to be the active caspase-3 and caspase-9. It is known that cell apoptosis is induced by the signaling pathway with which such an active caspase-3 and caspase-9 are involved. Accordingly, the apoptosis suppression effect rendered by LPP was analyzed.

(Induction of Caspase Cascade)

Caco-2/bbe cell was cultured for 24 hours in the presence of 0 μg/ml (control), 1 μg/ml or 10 μg/ml of LPP. Then, staurosporine, a protein kinase inhibitor, was added to the medium so as to give 1 μM. After adding staurosporine, the cell was collected 0 hour, 1 hour, 3 hours, 6 hours and 9 hours later, and the protein amount of inactive full-length caspase-9 and the protein amount of inactive full-length caspase-3 were analyzed by the western blot method.

Figure 14:
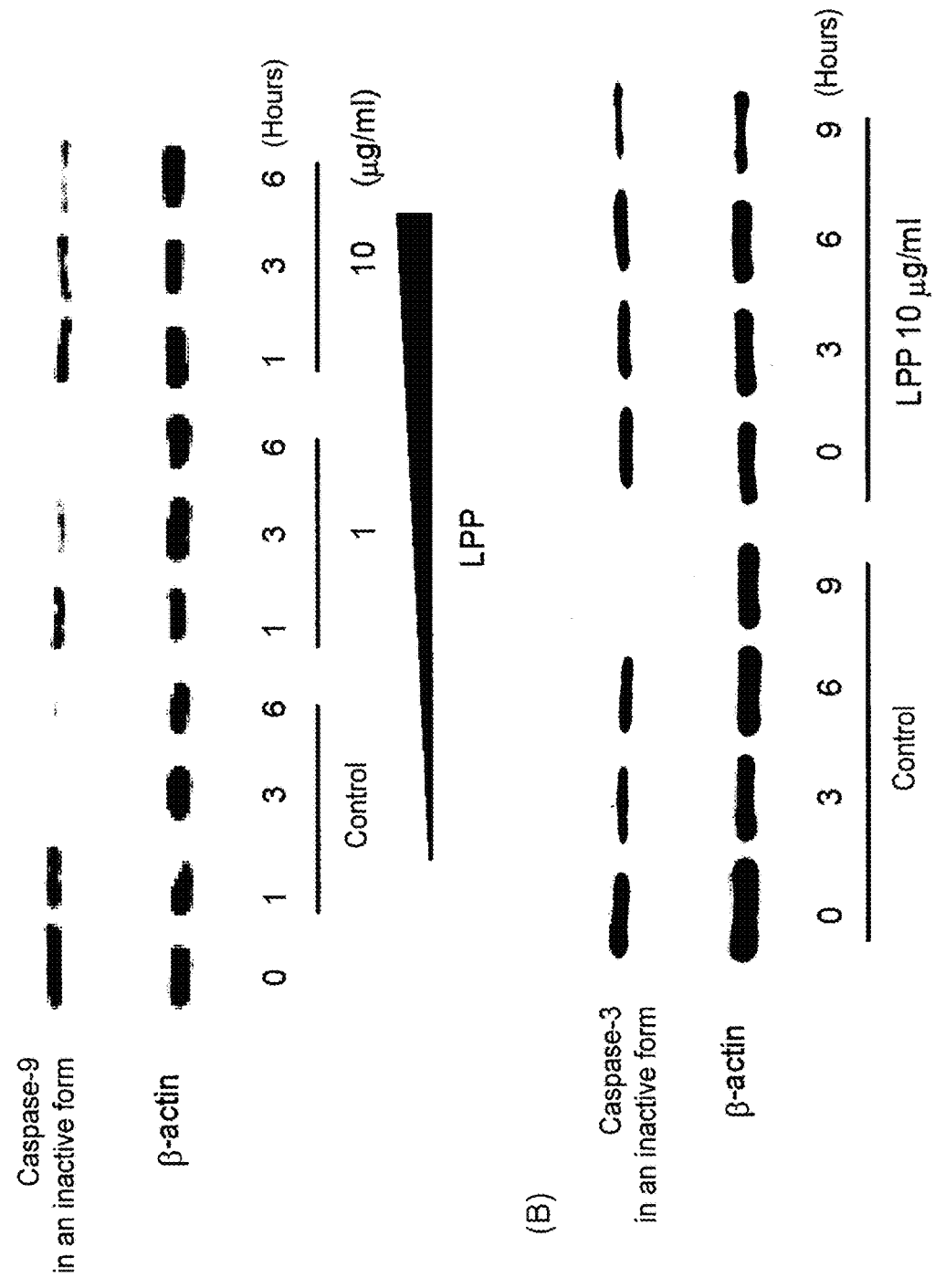
FIG. 14 is pictures showing western blot of Example 10.

In the control to which LPP was not added, the protein amounts of inactive full-length caspase-9 and inactive full-length caspase-3 were decreased by the addition of staurosporine (FIG. 14(A), (B)). This indicates that the post-translational modification occurs by the stimulation caused by staurosporine, whereby the active caspase-3 and caspase-9 are produced. On the other hand, in the LPP-added cell, when compared with the control, the protein amount decrease of inactive full-length caspase-9 and inactive full-length caspase-3 caused by the addition of staurosporine was suppressed (FIG. 14(A), (B)).

From this result, it was revealed that polyphosphoric acid suppresses the apoptosis caused by the caspase-involved signaling pathway.

Example 11

Enhancement of the Intestinal Tract Barrier Function by Chemically Synthesized Polyphosphoric Acid The intestinal tract permeability experiment on mannitol by ex vivo loop assay was carried out in the same manner as in Example 9 except that a chemically synthesized polyphosphoric acid (made by SIGMA-ALDRICH Corp., sodium phosphate glass, catalog No. "S4379", average polymerization degree of 45±5) (chemically synthesized polyphosphoric acid) was used in place of the enzymatically synthesized polyphosphoric acid, and the intestinal tract barrier function was evaluated.

Figure 15:
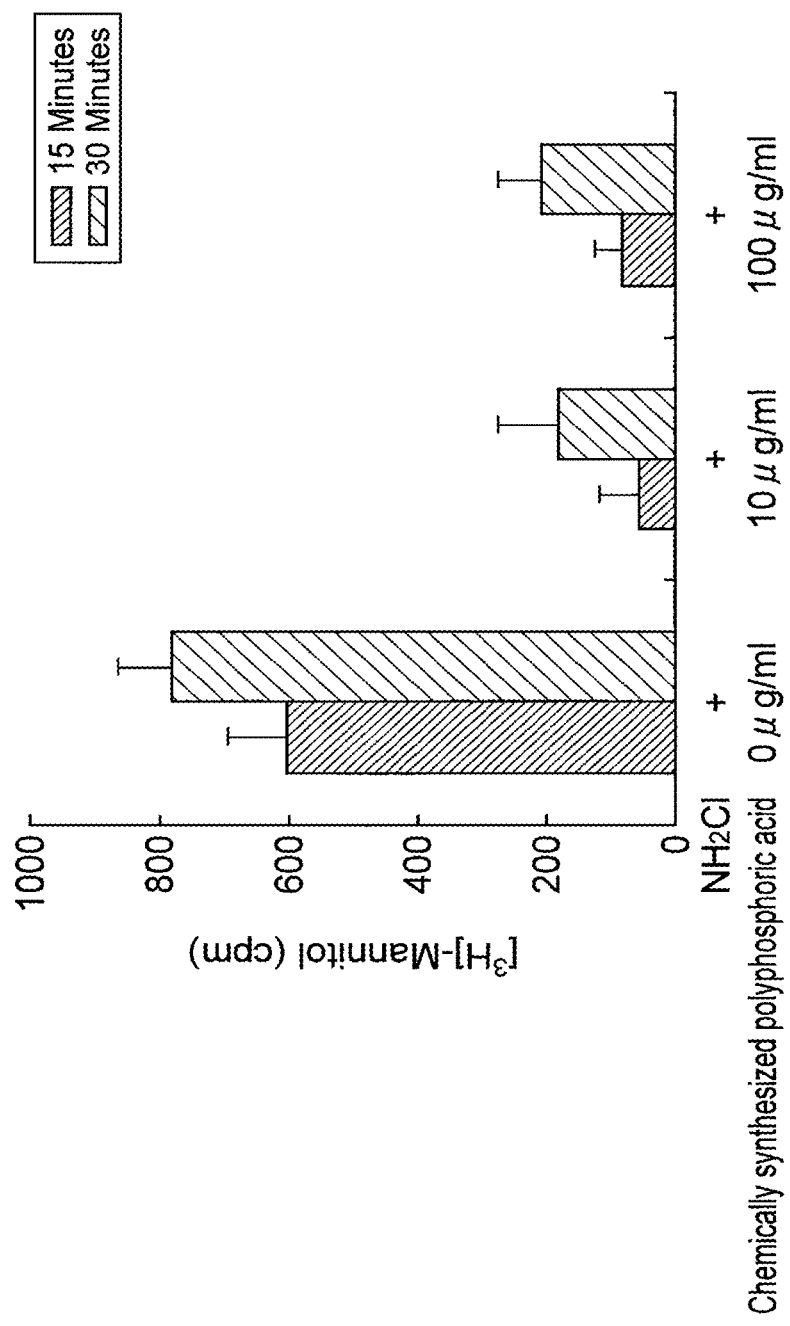
FIG. 15 is a graph showing the mannitol leakage in Example 11.

The graph of mannitol leakage is shown in FIG. 15. The data in FIG. 15 are all those obtained when the oxidative stress was applied by monochloramin. In the intestinal tract treated with the chemically synthesized polyphosphoric acid, the mannitol leakage was evidently suppressed compared with the intestinal tract treated only with PBS (FIG. 15). More specifically, it was indicated that the chemically synthesized polyphosphoric acid is also capable of recovering the intestinal tract barrier function or suppressing the decline of the intestinal tract barrier function.

Example 12

Interaction Between Polyphosphoric Acid and Integrin

Using a peptide antagonist of integrin, the interaction between polyphosphoric acid and integrin was analyzed. For the peptide antagonist of integrin, the peptide having the amino acid sequence of Gly-Arg-Gly-Asp-Thr-Pro (GRGDTP) (hereinafter also referred to as "GRGDTP") was used. GRGDTP has the sequence of Arg-Gly-Asp (RGD), which is recognized by integrin β.

The intestinal tract permeability experiment on mannitol by ex vivo loop assay was carried out in the same manner as in Example 9 and Example 11 except that GRGDTP was added in a concentration of 100 μg/ml, in addition to the enzymatically synthesized polyphosphoric acid or the chemically synthesized polyphosphoric acid, to the PBS solution to be filled in the intestinal tract, and the intestinal tract barrier function was evaluated.

Figure 16:
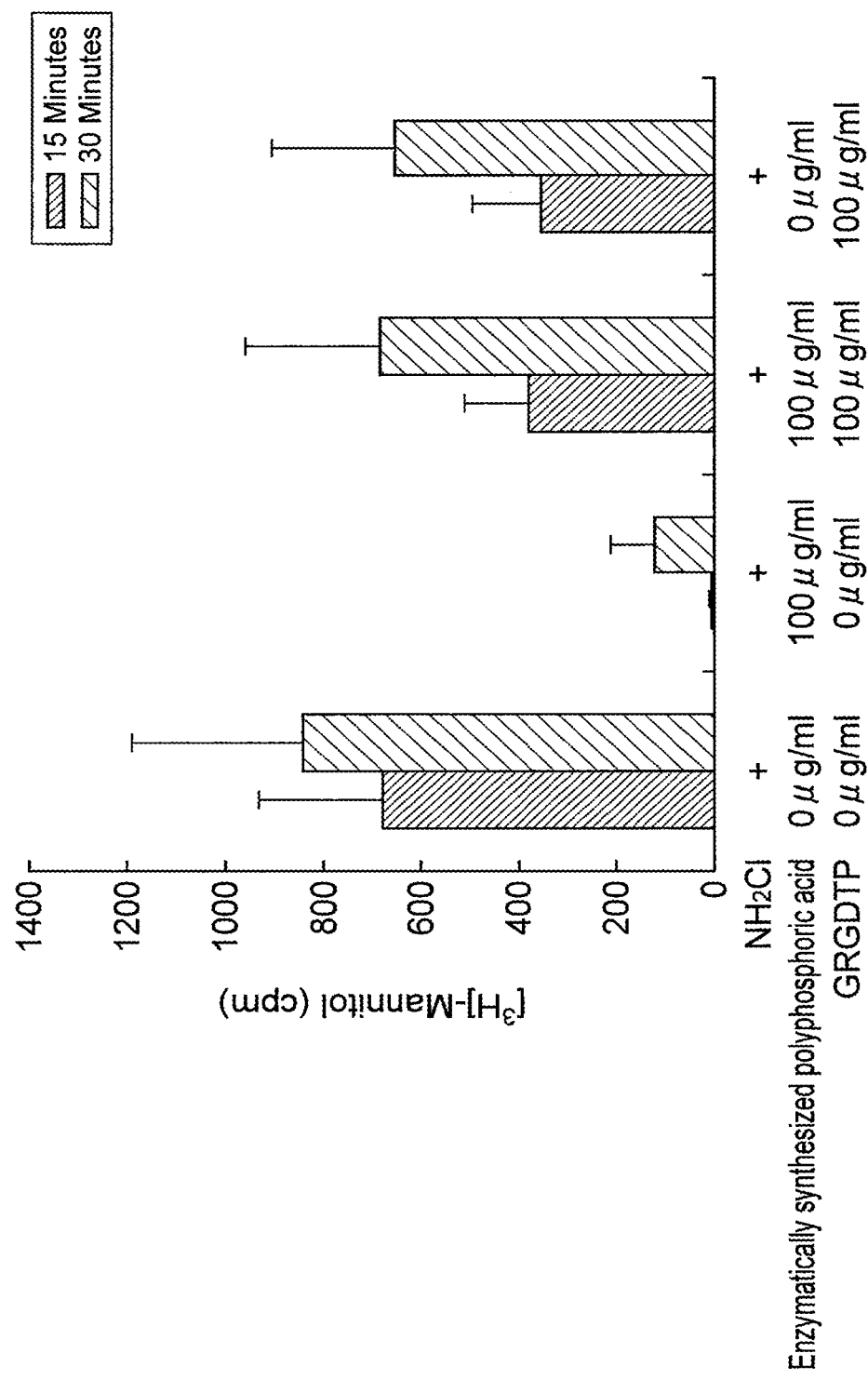
FIG. 16 is a graph showing the mannitol leakage in Example 12.
Figure 17:
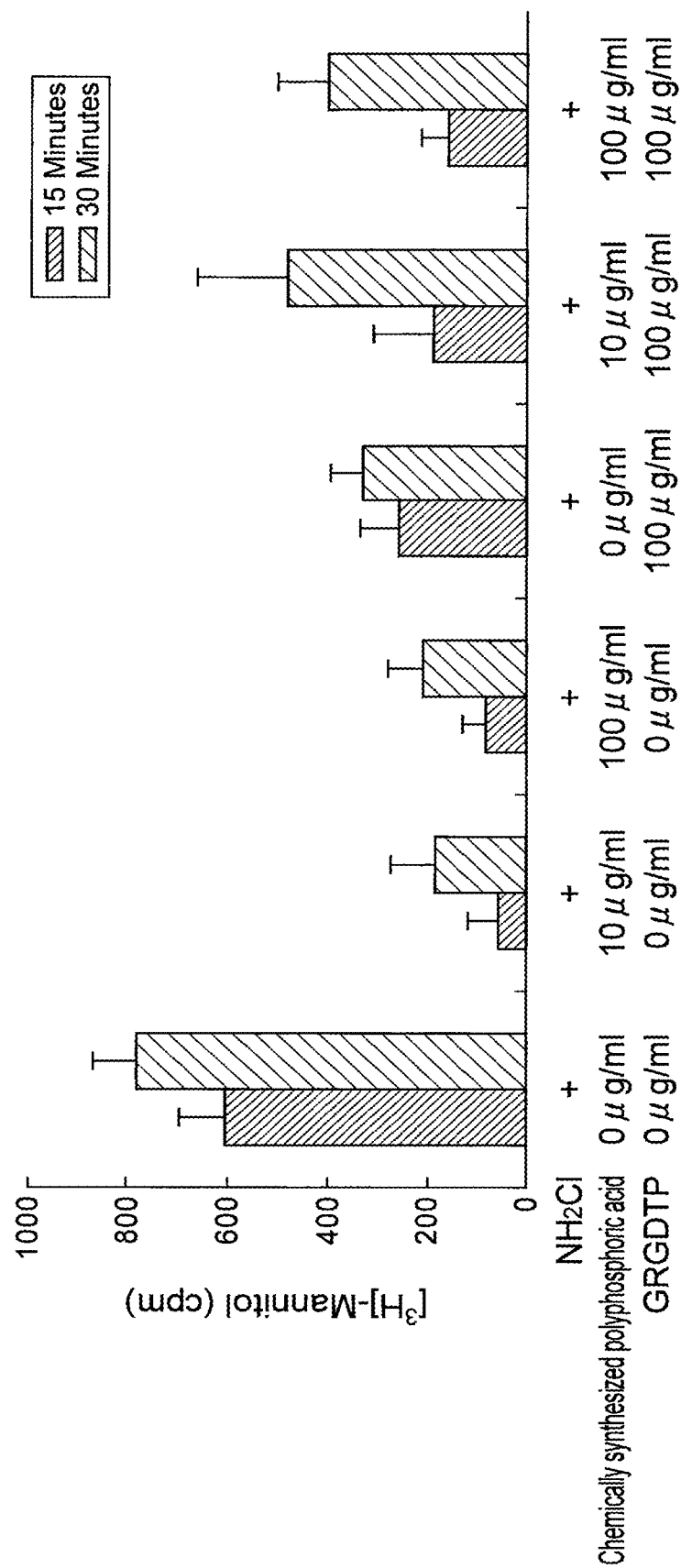
FIG. 17 is a graph showing the mannitol leakage in Example 12.

FIG. 16 shows the graph of mannitol leakage when the enzymatically synthesized polyphosphoric acid and GRGDTP were used in combination. FIG. 17 shows the graph of mannitol leakage when the chemically synthesized polyphosphoric acid and GRGDTP were used in combination. In the case where the enzymatically synthesized polyphosphoric acid and GRGDTP were used in combination, the recovery effect on intestinal tract barrier function or the decline suppression effect on intestinal tract barrier function rendered by the enzymatically synthesized polyphosphoric acid was remarkably inhibited (FIG. 16). Also, the case where the chemically synthesized polyphosphoric acid and GRGDTP were used in combination had the same result (FIG. 17). More specifically, it is indicated that the recovery effect on the intestinal tract barrier function or the decline suppression effect on intestinal tract barrier function rendered by polyphosphoric acid are inhibited by the bonding of GRGDTP to integrin which is competitive to that of polyphosphoric acid.

Integrin is a cell surface protein and a cell adhesion molecule involved with the adhesion of a cell and an extracellular matrix and the signal transduction from an extracellular matrix. The results of Example 12 indicate that polyphosphoric acid renders the recovery effect on intestinal tract barrier function or the decline suppression effect on intestinal tract barrier function through the activation of p38 MAPK pathway by bonding to integrin (integrin β) present in the intestinal tract lumen.

The invention claimed is:

1. A method of inducing expression of heat shock protein 27 in a subject, comprising
synthesizing a polyphosphoric acid or a pharmaceutically acceptable salt thereof thorough an enzymatic reaction with polyphosphate kinase (PPK), adenosine triphosphate (ATP) and adenosine diphosphate (ADP) in a reaction solution, wherein a larger amount of ADP than ATP is not present in the reaction solution,
filtering the polyphosphoric acid or the pharmaceutically acceptable salt thereof with a 10 kDa cut-off filter thereby obtaining a polyphosphoric acid or a pharmaceutically acceptable salt thereof that does not pass through the filter, and
administering to a subject in need thereof an effective amount of a composition comprising the polyphosphoric acid or the pharmaceutically acceptable salt thereof that does not pass through the filter,
wherein the polyphosphoric acid comprises a linear chain polyphosphoric acid of formula (1) or a branched chain polyphosphoric acid having a branch which further bonds to the side chain of a linear chain polyphosphoric acid represented by formula (1):

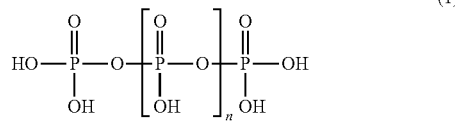

(1)

wherein n is an integer between 100 and 10,000.

2. The method according to claim 1, wherein the method protects an intestinal tract in the subject.

3. The method according to claim 1, wherein the method ameliorates an inflammatory bowel disease in the subject.

4. The method according to claim 1, wherein the method suppresses a decline in an intestinal tract barrier function or recovers an intestinal tract barrier function.

5. The method according to claim 1, wherein the polyphosphoric acid comprises the linear chain polyphosphoric acid of formula (1).

6. The method according to claim 1, wherein the polyphosphoric acid comprises the branched chain polyphosphoric acid having a branch which further bonds to the side chain of a linear chain polyphosphoric acid represented by formula (1).

7. A method of inducing expression of heat shock protein 27 in a subject, comprising
synthesizing a polyphosphoric acid or a pharmaceutically acceptable salt thereof thorough culturing a polyphosphoric acid-producing microorganism in a medium,
filtering the polyphosphoric acid or the pharmaceutically acceptable salt thereof with a 10 kDa cut-off filter thereby obtaining a polyphosphoric acid or a pharmaceutically acceptable salt thereof that does not pass through the filter, and
administering to a subject in need thereof an effective amount of a composition comprising the polyphosphoric acid or the pharmaceutically acceptable salt thereof that does not pass through the filter,
wherein the polyphosphoric acid-producing microorganism comprises one selected from the group consisting of *Lactobacillus rhamnosus* GG strain, *Lactobacillus brevis* SBC8803 strain, strains belonging to genera *Lactobacillus, Bifidobacterium, Enterococcus, Lactococcus, Pediococcus, Leuconostoc, Streptococcus, Bacteroidetes, Eubacterium*, and *Clostridium*, and
wherein the polyphosphoric acid comprises a linear chain polyphosphoric acid of formula (1) or a branched chain polyphosphoric acid having a branch which further bonds to the side chain of a linear chain polyphosphoric acid represented by formula (1):

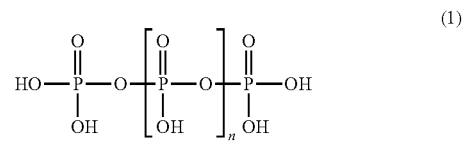

(1)

wherein n is an integer between 100 and 10,000.

8. The method according to claim 7, wherein the method protects an intestinal tract in the subject.

9. The method according to claim 7, wherein the method ameliorates an inflammatory bowel disease in the subject.

10. The method according to claim 7, wherein the method suppresses a decline in an intestinal tract barrier function or recovers an intestinal tract barrier function.

11. The method according to claim 7, wherein the polyphosphoric acid comprises the linear chain polyphosphoric acid of formula (1).

12. The method according to claim 7, wherein the polyphosphoric acid comprises the branched chain polyphosphoric acid having a branch which further bonds to the side chain of a linear chain polyphosphoric acid represented by formula (1).

13. A method of inducing expression of heat shock protein 27 in a subject, comprising
synthesizing a polyphosphoric acid or a pharmaceutically acceptable salt thereof thorough an enzymatic reaction with polyphosphate kinase (PPK), adenosine triphosphate (ATP) and adenosine diphosphate (ADP) in a reaction solution, wherein a larger amount of ADP than ATP is not present in the reaction solution, and
administering to a subject in need thereof an effective amount of a composition comprising the polyphosphoric acid or the pharmaceutically acceptable salt thereof,
wherein the polyphosphoric acid comprises a linear chain polyphosphoric acid of formula (1) or a branched chain polyphosphoric acid having a branch which further bonds to the side chain of a linear chain polyphosphoric acid represented by formula (1):

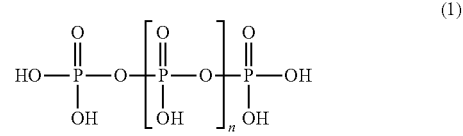

(1)

wherein n is an integer between 100 and 10,000, and
wherein the composition excludes polyphosphoric acid which permeates a filtration membrane with a molecular weight cut off of 10 kDa.

14. The method according to claim 13, wherein the method protects an intestinal tract in the subject.

15. The method according to claim 13, wherein the method ameliorates an inflammatory bowel disease in the subject.

16. The method according to claim 13, wherein the method suppresses a decline in an intestinal tract barrier function or recovers an intestinal tract barrier function.

17. The method according to claim 13, wherein the polyphosphoric acid comprises the linear chain polyphosphoric acid of formula (1).

18. The method according to claim 13, wherein the polyphosphoric acid comprises the branched chain polyphosphoric acid having a branch which further bonds to the side chain of a linear chain polyphosphoric acid represented by formula (1).

19. A method of inducing expression of heat shock protein 27 in a subject, comprising
synthesizing a polyphosphoric acid or a pharmaceutically acceptable salt thereof thorough culturing a polyphosphoric acid-producing microorganism in a medium, and
administering to a subject in need thereof an effective amount of a composition comprising the polyphosphoric acid or the pharmaceutically acceptable salt thereof,
wherein the polyphosphoric acid-producing microorganism comprises one selected from the group consisting of *Lactobacillus rhamnosus* GG strain, *Lactobacillus brevis* SBC8803 strain, strains belonging to genera *Lactobacillus, Bifidobacterium, Enterococcus, Lactococcus, Pediococcus, Leuconostoc, Streptococcus, Bacteroidetes, Eubacterium*, and *Clostridium*,
wherein the polyphosphoric acid comprises a linear chain polyphosphoric acid of formula (1) or a branched chain polyphosphoric acid having a branch which further bonds to the side chain of a linear chain polyphosphoric acid represented by formula (1):

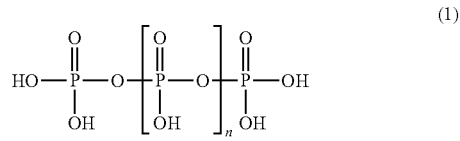

wherein n is an integer between 100 and 10,000, and
wherein the composition excludes polyphosphoric acid which permeates a filtration membrane with a molecular weight cut off of 10 kDa.

20. The method according to claim 19, wherein the method protects an intestinal tract in the subject.

21. The method according to claim 19, wherein the method ameliorates an inflammatory bowel disease in the subject.

22. The method according to claim 19, wherein the method suppresses a decline in an intestinal tract barrier function or recovers an intestinal tract barrier function.

23. The method according to claim 19, wherein the polyphosphoric acid comprises the linear chain polyphosphoric acid of formula (1).

24. The method according to claim 19, wherein the polyphosphoric acid comprises the branched chain polyphosphoric acid having a branch which further bonds to the side chain of a linear chain polyphosphoric acid represented by formula (1).

* * * * *

SEQUENCE LISTING

<160> NUMBER OF SEQ ID NOS: 1

<210> SEQ ID NO 1
<211> LENGTH: 6
<212> TYPE: PRT
<213> ORGANISM: Artificial
<220> FEATURE:
<223> OTHER INFORMATION: Integrin antagonist

<400> SEQUENCE: 1

Gly Arg Gly Asp Thr Pro
1               5